(12) United States Patent
Shachaf et al.

(10) Patent No.: US 11,185,278 B2
(45) Date of Patent: Nov. 30, 2021

(54) SYSTEM FOR IMAGING LESIONS ALIGNING TISSUE SURFACES

(71) Applicant: Orlucent, Inc., Los Gatos, CA (US)

(72) Inventors: Catherine M. Shachaf, Los Gatos, CA (US); Amit Shachaf, Palo Alto, CA (US)

(73) Assignee: Orlucent, Inc., Los Gatos, CA (US)

( * ) Notice: Subject to any disclaimer, the term of this patent is extended or adjusted under 35 U.S.C. 154(b) by 269 days.

(21) Appl. No.: 16/184,667

(22) Filed: Nov. 8, 2018

(65) Prior Publication Data

US 2019/0307391 A1  Oct. 10, 2019

Related U.S. Application Data

(63) Continuation of application No. 14/364,053, filed as application No. PCT/US2012/071246 on Dec. 21, 2012, now Pat. No. 10,165,976.

(Continued)

(51) Int. Cl.
| | |
|---|---|
| *A61B 6/00* | (2006.01) |
| *A61B 5/00* | (2006.01) |
| *G06T 7/73* | (2017.01) |
| *G06T 7/00* | (2017.01) |
| *H04N 5/235* | (2006.01) |

(Continued)

(52) U.S. Cl.
CPC ............ *A61B 5/444* (2013.01); *A61B 5/0071* (2013.01); *A61B 5/0077* (2013.01); *A61B 5/0082* (2013.01); *A61B 5/4887* (2013.01); *A61B 5/6833* (2013.01); *G06T 7/0012* (2013.01); *G06T 7/74* (2017.01); *H04N 5/235* (2013.01); *H04N 5/232122* (2018.08); *H04N 5/232123* (2018.08); *A61B 1/043* (2013.01); *A61B 5/0037* (2013.01); *A61B 5/443* (2013.01); *G06T 2207/10048* (2013.01);
(Continued)

(58) Field of Classification Search
CPC combination set(s) only.
See application file for complete search history.

(56) References Cited

U.S. PATENT DOCUMENTS

| | | |
|---|---|---|
| 5,717,959 A | 2/1998 | Takunaga |
| 6,091,983 A | 7/2000 | Alfano et al. |

(Continued)

FOREIGN PATENT DOCUMENTS

| | | |
|---|---|---|
| CN | 102099671 A | 6/2011 |
| JP | 2011133366 A | 7/2011 |

(Continued)

OTHER PUBLICATIONS

Rosenthal et al., "Use of fluorescent labeled anti-epidermal growth factor receptor antibody to image head and neck squamous cell carcinoma xenografts", Molecular Cancer Therapeutics, Apr. 3, 2007, pp. 1230-1238, vol. 6, No. 4, American Association of Cancer Research, Philadelphia, PA.

(Continued)

*Primary Examiner* — Joel F Brutus
(74) *Attorney, Agent, or Firm* — Dave Law Group LLC; Raj S. Dave

(57) ABSTRACT

Methods, compositions and systems are provided for the imaging of cavity/tissue lesions, including without limitation cavity/tissue malignant lesions, e.g. cancers of the skin, mouth, colon, digestive system cervix, bladder, lung, etc.

23 Claims, 14 Drawing Sheets

Related U.S. Application Data

(60) Provisional application No. 61/578,441, filed on Dec. 21, 2011.

(51) Int. Cl.
*H04N 5/232* (2006.01)
*A61B 1/04* (2006.01)

(52) U.S. Cl.
CPC .............. *G06T 2207/30088* (2013.01); *G06T 2207/30096* (2013.01); *Y10T 29/49716* (2015.01)

(56) References Cited

U.S. PATENT DOCUMENTS

| | | |
|---|---|---|
| 6,627,446 B1 | 9/2003 | Roach et al. |
| 6,863,650 B1 | 3/2005 | Irion |
| 7,842,466 B1 | 11/2010 | Kim et al. |
| 2002/0058864 A1 | 5/2002 | Mansfield et al. |
| 2004/0057094 A1 | 3/2004 | Olszak et al. |
| 2005/0026181 A1 | 2/2005 | Davis et al. |
| 2005/0118640 A1 | 6/2005 | Kureshy et al. |
| 2006/0127946 A1 | 6/2006 | Montagu et al. |
| 2006/0148028 A1 | 7/2006 | Noda et al. |
| 2006/0227325 A1 | 10/2006 | Rulison et al. |
| 2007/0020181 A1 | 1/2007 | Workman et al. |
| 2008/0032328 A1 | 2/2008 | Cline et al. |
| 2008/0317325 A1 | 12/2008 | Ortyn et al. |
| 2009/0130650 A1 | 5/2009 | Tan |
| 2009/0253991 A1 | 10/2009 | Balas et al. |
| 2009/0273447 A1 | 11/2009 | Selker et al. |
| 2010/0042004 A1 | 2/2010 | Dhawan |
| 2010/0121156 A1 | 5/2010 | Yoo |
| 2010/0204064 A1 | 8/2010 | Cho |
| 2010/0214430 A1 | 8/2010 | Boer et al. |
| 2011/0009163 A1 | 1/2011 | Fletcher et al. |
| 2011/0217207 A1 | 3/2011 | Fujimoto et al. |
| 2011/0117025 A1* | 5/2011 | Dacosta ............. G01N 21/6456 424/9.6 |
| 2011/0117028 A1 | 5/2011 | Zharov |
| 2011/0264209 A1 | 10/2011 | Wiechmann et al. |
| 2011/0278554 A1 | 11/2011 | Ma et al. |
| 2011/0294543 A1 | 12/2011 | Lapstun et al. |
| 2012/0068855 A1 | 3/2012 | Matsumara et al. |
| 2012/0083005 A1* | 4/2012 | Malecki ............. G01N 33/6857 435/7.23 |
| 2012/0083761 A1 | 4/2012 | Malecki et al. |
| 2012/0093730 A1 | 4/2012 | Malecki et al. |
| 2012/0123205 A1* | 5/2012 | Nie ..................... A61B 5/0075 600/109 |
| 2012/0330284 A1 | 12/2012 | Hyde et al. |
| 2013/0100272 A1 | 4/2013 | Price et al. |

FOREIGN PATENT DOCUMENTS

| | | |
|---|---|---|
| JP | 2011521237 A | 7/2011 |
| WO | 1990013091 A1 | 11/1990 |
| WO | 2003/067230 A1 | 8/2003 |
| WO | 2011112559 A2 | 9/2011 |

OTHER PUBLICATIONS

Balch et al., "Final Version of the American Join Committee on Cancer staging system for Cutaneous Melanoma", Journal of Clinical Oncology, Aug. 2001, pp. 3635-3648, vol. 19, No. 16, American Society of Clinical Oncology, Alexandria, VA.

Breslow, "Thickness, Cross-sectional Areas and Depth of Invasion in the Prognosis of Cutaneous Melanoma" Annals of Surgery, Nov. 1970, pp. 902-908, 172(5), Lippincott, Williams, and Wilkins, Philadelphia, PA.

Carmeliet et al., "Angiogenesis in Cancer and Other Disease", Nature, Sep. 14, 2000, pp. 249-257, vol. 407, Springer Nature, Basingstoke, United Kingdom.

Chatziioannou, "Instrumentation for Molecular Imaging in Preclinical Research: Micro-PET and Micro-SPECT", ATS Journals, Aug. 1, 2005, pp. 533-536, 510-511, vol. 2, No. 6, American Thoracic Society, New York, NY.

Ellis et al., "Synopsis of Angiogenesis Inhibitors in Oncology", Oncology, May 1, 2002, pp. 14-22, vol. 16 Iss. 5, UBM plc, London, United Kingdom.

Heasley et al., "Pathology of malignant melanoma", Surgical Clinics, Dec. 1, 1996, pp. 1223-1255, vol. 76 Iss. 6, Elsevier Inc, Atlanta, GA.

Folkman, "Tumor Angiogenesis: Therapeutic Implications.", The New England Journal of Medicine, Nov. 18, 1971, pp. 1182-1186, Massachusetts Medical Society, Waltham, MA.

Folkman et al., "Tumor Angiogenesis: Effect on Tumor Growth and Immunity", Fundamental Aspects of Neoplasia, 1975, pp. 401-412, Springer, Berlin, Heidelberg.

Matsumoto et al., "Performance Characteristics of a New 3-Dimensional Continuous-Emission and Spiral-Transmission High-Sensitivity and High-Resolution PET Camera Evaluated with the NEMA NU Feb. 2001 Standard", The Journal of Nuclear Medicine, Jan. 2006, 83-90, vol. 47, No. 1, Society of Nuclear Medicine and Molecular Imaging, Reston, VA.

Srivastava et al., "Neovascularization in human cutaneous melanoma: a quantitative morphological and Doppler ultrasound study", European Journal of Cancer, Oct. 1986, pp. 1205-1209, vol. 22, Issue 10, Elsevier Inc, Atlanta, GA.

Gooitzen et al., "Intraoperative tumor-specific fluorescence imaging in ovarian cancer by folate receptor-a targeting: first in-human results", Nature Medicine, pp. 1315-1220, Oct. 2011, vol. 17, No. 10, Springer Nature, Basingstoke, United Kingdom.

Richter et al., "Comparison of Fluorescent Tag DNA Labeling Methods Used for Expression Analysis by DNA Microarrays", BioTechinques, Sep. 2002, pp. 620-630, vol. 33, No. 3, National Center for Biotechnology Information, Bethesda MD.

* cited by examiner

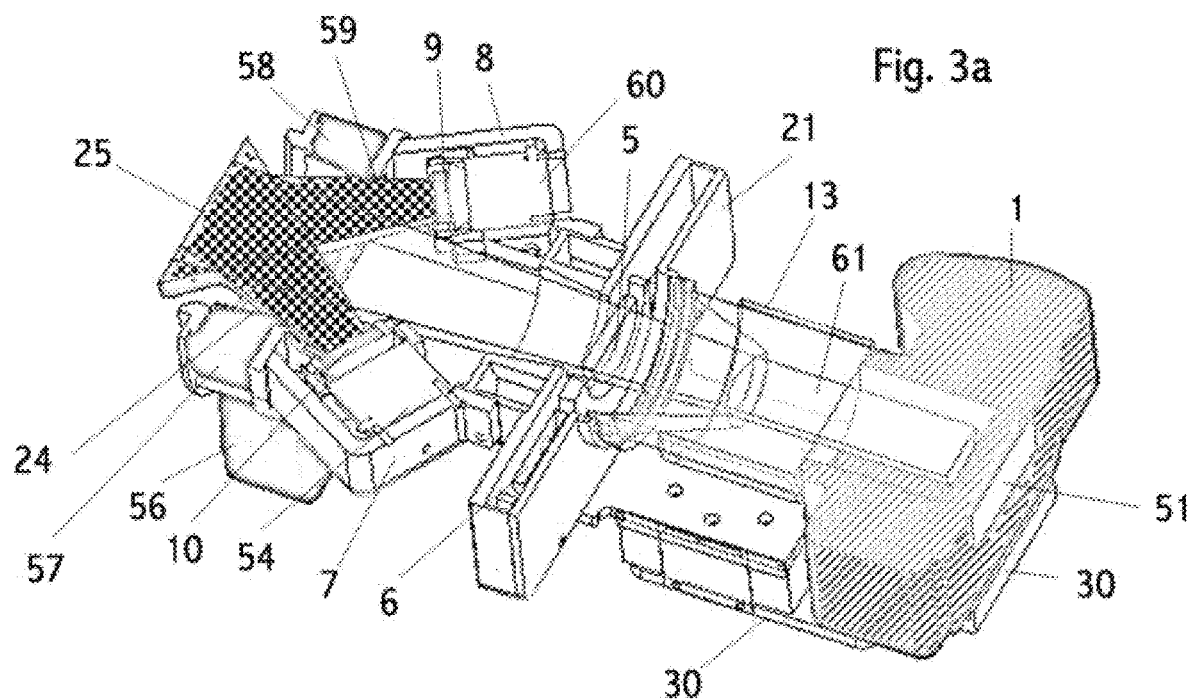
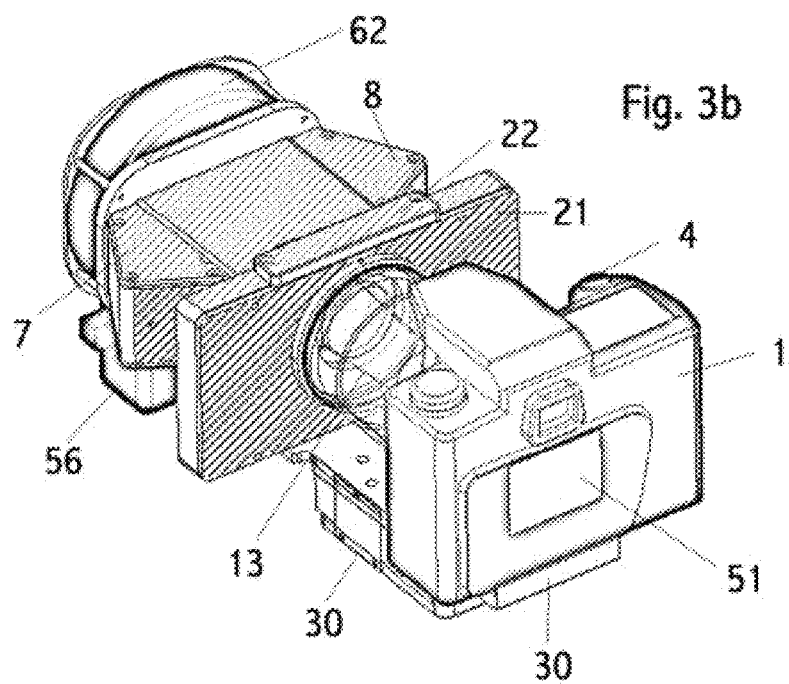

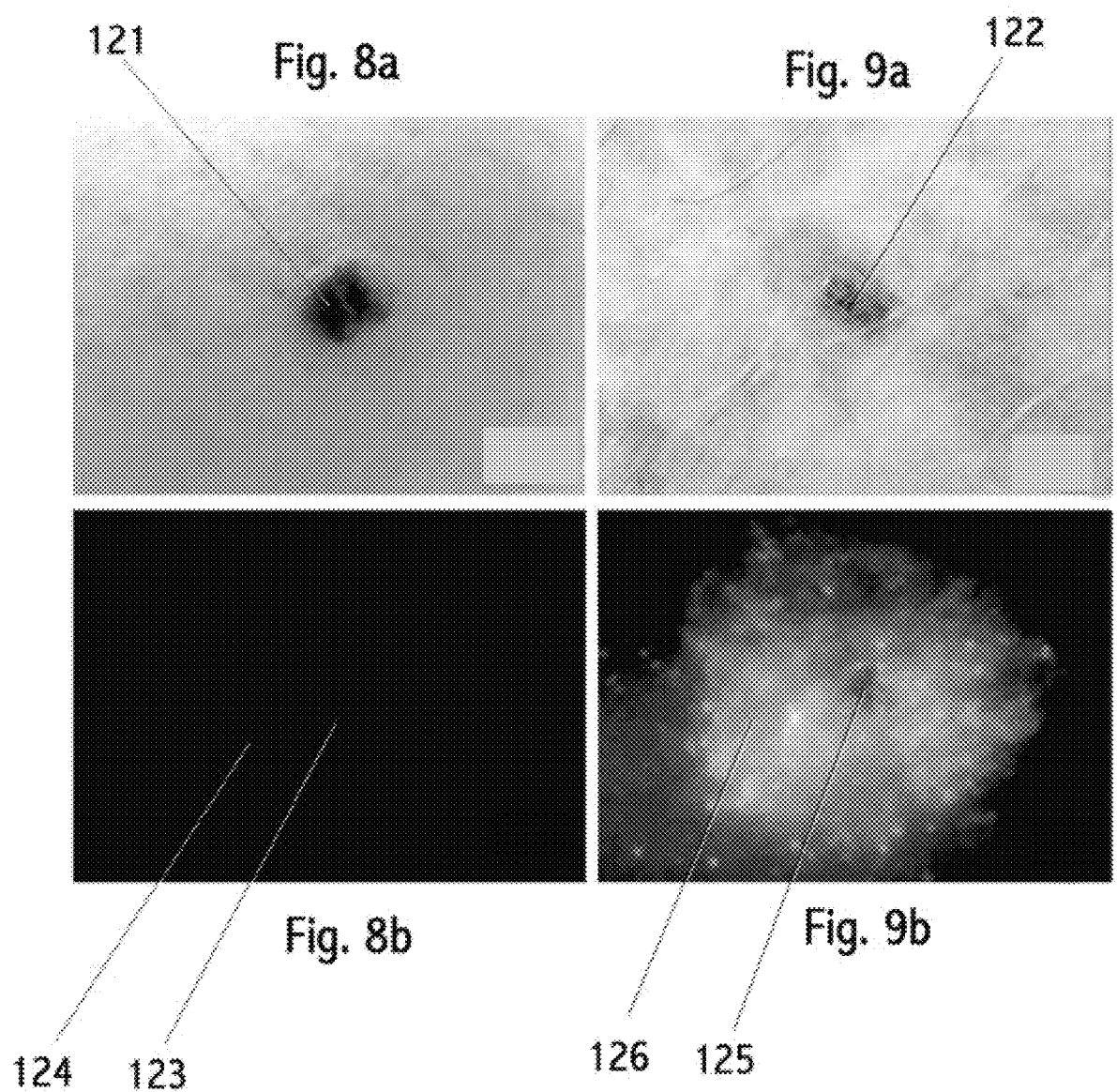

SYSTEM FOR IMAGING LESIONS ALIGNING TISSUE SURFACES

CROSS REFERENCE

This application claims benefit and is a continuation of application Ser. No. 14/364,053 filed Jun. 9, 2014, which is a 371 application and claims the benefit of PCT Application No. PCT/US2012/071246, filed Dec. 21, 2012, which claims benefit of U.S. Provisional Patent Application No. 61/578, 441, filed Dec. 21, 2011, which applications are incorporated herein by reference in their entirety.

FIELD OF THE INVENTION

The field of this invention is medical diagnostic devices and methods. More specifically, imaging, analysis and diagnosis of lesions aligning tissue surfaces, such as cancers of the skin, mouth, colon, digestive system cervix, bladder, lung, etc.

BACKGROUND

Cancer is a leading cause of death worldwide and accounted for 7.6 million deaths (around 13% of all deaths) in 2008. Melanoma is an example of a cancer aligning the skin tissue surface and used here as an example. About 10% of all people with melanoma have a family history of melanoma. One is at increased risk of developing melanoma if there is a family history of melanoma in one or more of your first-degree relatives (parent, brother or sister, or child).

Melanoma is currently the sixth most common cancer in American men and the seventh most common in American women. The median age at diagnosis is between 45 and 55, although 25% of cases occur in individuals before age 40. It is the second most common cancer in women between the ages of 20 and 35, and the leading cause of cancer death in women ages 25 to 30.

Melanoma is the most aggressive form of skin cancer. If it is recognized and treated early it is almost always curable, but if it is not, the cancer can advance and spread to other parts of the body, where it becomes hard to treat and can be fatal. While it is not the most common of the skin cancers, it causes the most deaths. The American Cancer Society estimates that at present, about 120,000 new cases of melanoma in the US are diagnosed in a year. In 2010, about 68,130 of these were invasive melanomas, with about 38,870 in males and 29, 260 in women.

There are four basic types of melanoma which differ in frequency and location in the body. All melanomas pose the same level of risk, based on the following factors: Tumor depth (Breslow depth), Mitotic index (cells that are dividing within the melanoma), presence or absence of ulceration, number of regional lymph nodes containing melanoma, and extent of cancer spread in the regional lymph nodes.

Superficial spreading melanoma is the most common type of melanoma, representing about 70% of all cases. As its name suggests, it spreads along the epidermis for a period of months to years before penetrating more deeply into the skin. The melanoma appears as a flat or barely raised lesion, often with irregular borders and variations in color. Lesions most commonly appear on the trunks of men, the legs of women, and the upper back of both sexes. The earliest sign of a new superficial spreading melanoma is darkening in one part of a pre¬existing mole or the appearance of a new mole on unaffected normal skin.

Nodular melanoma represents 15 to 30% of all melanomas. It grows deeper more quickly than other types of melanoma, and is found most often on the trunk or head and neck. The melanoma usually appears as a blue-black, dome-shaped nodule, although 5% of lesions are pink or red. Nodular melanoma is more common in men than women.

Lentigo maligna melanoma arises from a pre-existing lentigo, rather than a mole, and accounts for approximately 5% of all melanoma cases. This type of melanoma typically takes many years to develop. It occurs most often in older adults, usually on the face and other chronically sun-exposed areas. These melanomas are generally large, flat, tan-colored lesions containing differing shades of brown, or as in other melanomas, black, blue, red, gray, or white.

Acral lentiginous melanoma accounts for less than 5% of all melanomas but is the most common melanoma in African Americans and Asians; although this may also occur in light-skinned (Caucasian) individuals. The disease typically appears on the palms, soles, or under the nails. Lesions are usually tan, brown, or black, with variations in color and irregular borders. Because of the misconceptions that melanomas only occur in sun-exposed areas, and that dark-skinned and Asian people are not at risk for melanoma, these melanomas are often discovered later than other forms of melanoma. A tendency to mistake the early signs of acral lentiginous melanoma for bruises or injuries to the palms, soles, or nailbeds may further delay diagnosis.

Early detection of melanoma is critical for treatment and survival. When melanoma is found and treated early, the chances for long-term survival are excellent. Five-year survival rates for patients with early-stage (Stage I) melanoma exceed 90 to 95%. As melanoma progresses, it becomes increasingly more devastating and deadly. In later-stage disease, 5-year survival rates drop to less than 85%. With early detection, survival rates have improved steadily in recent years, and 85% of diagnosed patients enjoy long-term survival after simple tumor surgery.

The first sign of melanoma is often a change in the size, shape, or color of an existing mole or the appearance of a new mole. Since the vast majority of primary melanomas are visible on the skin, there is a good chance of detecting the disease in its early stages. However, changes in size, shape, or color of an existing mole or the appearance of a new mole is not always conclusive of presence of melanoma in a mole. Men most commonly develop melanoma on the trunk, particularly the back, and women on the legs or arms.

If the primary care physician suspects one may have melanoma, one will be referred to a dermatologist, a medical oncologist, or a surgical oncologist. To make a definitive diagnosis, they will perform examinations and tests. The doctor will first take a complete medical history to learn about ones symptoms and risk factors. Your age, time since your first concern, changes in features, sun burns, family history of atypical moles or skin cancer, particularly melanoma. Complete skin examination. Dermoscopy, Biopsy, Lymph node examination, chest x-ray, CT scan, Magnetic resonance imaging (MRI), Serum lactate dehydrogenase (LDH).

Melanoma is staged is based on the risk factors most important in determining prognosis. They include: Tumor thickness (also known as Breslow thickness): how deeply the tumor has penetrated the skin. Thickness is measured in millimeters (mm). Thinner tumors carry a more favorable prognosis than thicker tumors. The thicker the tumor, the greater the risk of tumor metastasis. The presence or absence of tumor ulceration: A condition in which the epidermis that covers a portion of the primary melanoma is not intact.

Ulcerated tumors pose a greater risk for metastatic disease than tumors that are not ulcerated. Mitoses: Active cell division of the tumor and can be defined in terms of number. This is determined by the pathologist. The more mitoses, the more aggressive the tumor growth. Metastatic lymph nodes. The greater the number of lymph nodes containing melanoma, the less favorable the prognosis. Whether metastasis to the lymph nodes is microscopic or macroscopic. Micrometastases are tiny tumors. They can be detected only by microscopic evaluation after sentinel lymph node biopsy or elective lymph node dissection. Macrometastases can be felt during physical examination or seen by the naked eye when inspected by a surgeon or pathologist. Their presence is confirmed by lymph node dissection or when the tumor is seen to extend beyond the lymph node capsule. Macrometastases carry a less favorable prognosis than micrometastases. The site of distant metastasis. Distant metastases to the skin, the subcutaneous tissue, or distant lymph nodes carry a relatively better prognosis than distant metastases to any other site in the body. Level of serum lactate dehydrogenase (LDH). LDH is an enzyme found in the blood and many body tissues. Elevated LDH levels usually indicate the presence of metastatic disease—and a less favorable prognosis than normal LDH levels.

The TNM Staging System was created by the American Joint Committee on Cancer (AJCC). The system defines cancer stage by describing:
T: the features of the primary tumor. The three distinguishing features are tumor thickness, mitoses, and ulceration. Tumor thickness (also known as Breslow depth) is measured in millimeters (mm).
N: the presence or absence of tumor spread to nearby lymph nodes
M: the presence or absence of metastasis to distant sites
Revised TNM Classification
Abbreviations: N/A, not applicable; LDH, lactate dehydrogenases.

| T Classification | Thickness | Ulceration Status |
|---|---|---|
| Tis | N/A | N/A |
| T1 | ≤1.0 mm | a: w/o ulceration and mitosis < $1/mm^2$ |
|  |  | b: with ulceration and mitosis ≥ $1/mm^2$ |
| T2 | 1.01-2.0 mm | a: w/o ulceration |
|  |  | b: with ulceration |
| T3 | 2.01-4.0 mm | a: w/o ulceration |
|  |  | b: with ulceration |
| T4 | >4.0 mm | a: w/o ulceration |
|  |  | b: with ulceration |

| N Classification | # of Metastatic Nodes | Nodal Metastatic Mass |
|---|---|---|
| N0 | No evidence of lymph node metastasis | |
| N1 | 1 node | a: micrometastasis |
|  |  | b: macrometastasis |
| N2 | 2-3 nodes | a: micrometastasis |
|  |  | b: macrometastasis |
|  |  | c: In transit metastases/satellites without metastatic nodes |
| N3 | 4 or more metastatic nodes, or matted nodes, or in-transit metastases/satellites and metastatic nodes | |

| M Classification | Site | Serum LDH |
|---|---|---|
| M0 | No evidence of metastasis to distant tissues or organs | |
| M1a | Distant skin, subcutaneous or nodal metastases | Normal |
| M1b | Lung metastases | Normal |
| M1c | All other visceral metastases | Normal |
|  | Or any distant metastases | Elevated |

One of the most important factors in staging melanoma—and in determining treatment and prognosis—is how deeply the tumor has penetrated the skin. Tumor depth is described in two ways: Breslow thickness is a method of measuring how deeply the primary tumor has penetrated the skin, regardless of anatomic layer. Tumor penetration is measured in millimeters (mm) from the epidermis to the deepest point of penetration. (1.0 mm=0.04 inch, or less than 1/16 inch.) Breslow thickness has replaced Clark level as a more accurate measurement of tumor depth and more predictive of prognosis. The thicker the tumor, the greater the chance it has metastasized to regional lymph nodes or distant sites.

Clark level is a method of measuring how deeply the primary tumor has penetrated the skin based on anatomic layer. The deeper the layer of penetration, the greater the chance the tumor has metastasized to regional lymph nodes or distant sites. Since skin thickness varies throughout the body, Clark level is considered to be less accurate than Breslow thickness in describing tumor penetration. In fact, in the new American Joint Committee on Cancer (AJCC) staging system for melanoma, Clark level is no longer considered a secondary characteristic of Stage I tumors no more than 1.0 mm thick. This has been replaced with mitoses.

Clark level I. The tumor is located only in the lowest layer of the epidermis, known as the dermo-epidermal junction. Level I is also known as melanoma in situ. Clark level II. The tumor has partially penetrated the papillary dermis, the loose connective tissue beneath the epidermis. Clark level III. The tumor has completely penetrated and filled the papillary dermis. Clark level IV. The tumor has penetrated through the papillary dermis to the dense connective tissue of the reticular dermis. Clark level V. The tumor has penetrated through the reticular dermis to the subcutaneous tissue, the fatty layer beneath the skin.

Melanoma is now grouped into the following stages according to the revised TNM staging system:

Stage 0 melanoma involves the epidermis but has not reached the underlying dermis. This stage is also called melanoma in situ (TisNOMO). Stage 0 melanoma is very early stage disease known as melanoma in situ (Latin for "in place"). Patients with melanoma in situ are classified as Tis (tumor in situ). The tumor is limited to the epidermis with no invasion of surrounding tissues, lymph nodes, or distant sites. Melanoma in situ is considered to be very low risk for disease recurrence or spread to lymph nodes or distant sites.

Stage I melanoma is characterized by tumor thickness, presence and number of mitoses, and ulceration status. There is no evidence of regional lymph node or distant metastasis.

There are two subclasses of Stage I melanoma.

Stage IA: T1aNOMO (tumor less than or equal to 1 mm, no ulceration, and no mitoses). Stage IB: T1 bNOMO or T2aNOMO (tumor less than or equal to 1 mm, with ulceration or mitoses).

Stage I melanomas are localized tumors. This means the primary tumor has not spread to nearby lymph nodes or distant sites. Stage I melanomas are considered to be low-risk for recurrence and metastasis.

Stage I melanomas are defined by two primary characteristics:

Tumor thickness (known as Breslow depth): how deeply the tumor has penetrated the skin. Thickness is measured in millimeters (mm). Ulceration: a condition in which the epidermis that covers a portion of the primary melanoma is not intact. Ulceration is determined by microscopic evaluation of the tissue by a pathologist, not by what can be seen with the naked eye. Mitoses: A condition of the cells being in a state of active division. Mitoses are determined by microscopic evaluation by a pathologist, not what can be seen with the naked eye, similar to ulceration. It will be defined as "present or not present" and should include a number of mitoses per mm2. The designation of Clark level measures the depth of invasion according to the number of layers of skin the tumor has penetrated. There are five anatomic layers of the skin: Level I: epidermis. Levels 11-IV: dermis. Level V: the subcutis.

Clark level is no longer considered by the new American Joint Committee on Cancer (AJCC) staging system for melanoma, as a secondary characteristic of Stage I tumors no more than 1.0 mm thick. This has been replaced with mitoses.

Subclasses of Stage I Melanoma

Stage IA (T1 aNOMO) T1a: the tumor is no more than 1.0 millimeter (mm) thick, with no ulceration and no mitoses. NO: the tumor has not spread to nearby lymph nodes. MO: the tumor has not spread to sites distant from the primary tumor. Stage IB (T1 bNOMO or T2aNOMO). T1b: the tumor is no more than 1.0 mm thick, with ulceration or presence of >1 mitoses. T2a: the tumor is 1.01-2.0 mm thick, with no ulceration. NO: the tumor has not spread to nearby lymph nodes. MO: the tumor has not spread to sites distant from the primary tumor.

Stage II melanoma is also characterized by tumor thickness and ulceration status. There is no evidence of regional lymph node or distant metastasis.

There are three subclasses of Stage ii melanoma.

Stage MA: T2bNOMO or T3aNOMO

Stage II B: T3bNOMO or T4aNOMO

Stage IIC: T4bNOMO

Stage III melanoma is characterized by the level of lymph node metastasis. There is no evidence of distant metastasis.

There are three subclasses of Stage ill melanoma.

Stage MIA: T1-T4a N1aMO or T1-T4aN2aMO

Stage IIIB: T1-T4bN 1aMO, T1-T4bN2aMO, T1-T4aN 1bMO, T 1-T4aN2bMO, or T1-T4a/bN2cMO Stage MIC: T1-4bN 1bNO, T1-4bN2bMO, or T1-4a/bN3MO Stage IV melanoma is characterized by the location of distant metastases and the level of serum lactate dehydrogenase (LDH).

Stage IV melanomas include any T or N classification. For details, see Stage IV.

Treatments are available for all people with melanoma. In many cases, the standard treatment is surgery to remove the tumor and a surrounding area of normal-appearing skin. Sometimes surgery is followed by additional therapy such as immunotherapy, chemotherapy, radiation, or a combination of these treatments. Chemotherapy and immunotherapy are also used to treat advanced or recurrent melanoma.

Tumors need blood flow to grow bigger than 2-3 mm. Judah Folkman first articulated the importance of angiogenesis for tumor growth in 1971. He stated that the growth of solid tumors remains restricted to 2-3 mm in diameter until the onset of angiogenesis. Tumors need oxygen and nutrients. For the first 2 mm of their growth (-one million cells) tumors get their oxygen and nutrients from the host capillaries and extracellular fluid. As they outgrow the host supply they start making their own blood vessels. Cancers "persuade" the existing host capillaries to sprout, change direction and grow throughout the tumor. To do this, they secrete growth factors—angiogenic factors.

Angiogenesis (neoangiogenesis) is a multistep process, which is regulated by a balance between pro- and antiangiogenic factors. Microtumor foci remain dormant until a biological event occurs to trigger growth beyond the 2 mm stage/size. One trigger is an insufficient nutrient supply resulting in hypoxic cells. State-of-the-art clinical PET scanners, are able to detect tumor foci with a resolution of 3-4 mm. Preclinical animal scanners allow for resolutions in the 1 mm range in small rodents.

Vascularization in melanoma occurs and melanoma becomes metastatic (>0.75 mm). Human malignant melanoma is a highly metastatic tumor with poor prognosis and high resistance to treatment. It progresses through different steps: nevocellular nevi, dysplastic nevi (when these two entity can be identified as primary events in melanocytic neoplasia progression), in situ melanoma, radial growth phase melanoma (Breslow index <0.75 mm), vertical growth phase melanoma (index >0.75 mm), and metastatic melanoma. Breslow's depth is used as a prognostic factor in melanoma of the skin. It is a description of how deeply tumor cells have invaded. Melanomas in the vertical growth stage phase are metastatic.

Primary melanoma tumor grows horizontally through the epidermis (non-invasive phase); over time, a vertical growth phase component intervenes and melanoma increases its thickness and invades the dermis (invasive phase). Once a vertical growth phase has developed, there is a direct correlation between the tumor thickness and the number of metastases.

Blood flow occurs in melanoma index >0.8 mm. To correlate melanoma thickness and angiogenesis, the blood flow in 71 primary skin melanomas were investigated using a 10 MHz Doppler ultrasound flowmeter. Flow signals were analyzed on an Angioscan-I I spectrum analyzer. Doppler flow signals were detected in 44 tumors, with a close relationship to Breslow's tumor thickness. No blood flow signal was detected in 27 lesions and 25 of these had a tumor thickness of 0.8 mm or less. Ninety-seven percent of tumors of thickness >0.8 mm had detectable Doppler flow signals. This study indicates the development of a neovascular bed as the tumor thickness approaches 0.8 mm. An additional study of tumor blood flow in 36 patients, 38 with malignant melanomas using Doppler Ultrasound flowmetry showed that tumor blood flow can be detected in most melanomas more than 0.9 mm thick, and is absent in most melanomas less than this thickness Cancer starts in a single cell. Cells accumulate genetic changes and become abnormal. During the early stages of tumor development first a micro tumor lesion is formed. At the second stage a tumor lesion is formed which expands beyond the size of the micro lesion. In the final stage tumor cells are released to the circulatory system in the process of metastasis.

Tumors remain dormant as microfoci in the body. At the stage of a micro tumor lesion, signals from the immune system can hold a micro tumor in check in a state of tumor dormancy by the tumor inability to grow beyond it's local macroenvironment. In this state, the level of cell proliferation is in balance to the level of cell death. As tumors accumulate additional genetic changes, they are able to disrupt this balance and grow beyond microfoci and the macroenvironment. This balanced state is overturned when the signals originating from the tumor increase overpowering the signals from the immune system. Tumor cells secret signaling proteins to the tumor microenvironment and macroenvironment. During this stage emerging tumors signal to the macroenvironmet the need, to expand into additional space and additional nutrient as well as oxygen required for expanded growth. These signals prepare the tumor environment for expanded tumor growth (increasing space) and for an increase in nutrient supply (angiogenesis). The process is mediated by growth factors, cytokines and other activations proteins released from the tumor cells or from the tumor macro/micro environment during tumor expansion.

These processes can be investigated by testing the tissue surrounding a tumor (macro environment-tissue surrounding the diseased tissue). Often this environment may be difficult to study, especially if the tumor is embedded deep in a tissue. However, tumor growths in the proximity of the tissue cavity/surface compartment are good candidates to this type of investigation. Examples of such tumors can be: skin cancers, mouth cancer, lung cancer, colon cancer, digestive system cancer, cervical cancer, bladder cancer, etc.

The ideal medical diagnostic procedure and tools would have the following characteristics: is minimally invasive or non-invasive; permits early stage disease detection; permits early body response to a new antigen; permits early body response to a foreign antigen, monitors disease development and progression; investigates the macro environment of the diseased cell and/or tissue as indication of presence of disease; is easy to use, low cost, provides a quick test to perform; can be performed by someone other than the physician; operates independent of skin color or ethnicity; provides immediate test results, provides consistency of results, works for a wide range of lesion types and body locations; is minimally dependent on human interpretation; is a simple test—minimal training necessary; provides automated or machine-assisted medical documentation, such as photographs or quantified test metrics; provides automated or machine-assisted electronic medical record keeping, such as machine readable codes on samples and files that directly tie to patient, doctor and date; operates independent of visual cues such as, color, shape and size; can identify melanoma in amelanotic skin lesion; and/or can identify melanoma in small lesions, less than 5 mm. Current technology has weaknesses in all or some of the above areas.

Also, the prior art uses an industrial camera connected to a computer. This arrangement is either impossible to hand hold, is too cumbersome to realistically handhold, or is difficult to consistently place in the correct position.

Prior art uses a fixed focal length lens, which only works when the camera can be placed a fixed distance from the subject. When using fluorescent biomarkers it is preferable to block all ambient and stray light from entering the optical path between the camera optics and the patient's skin. Therefore, some kind of physical light shield or light baffle is employed. This light baffle is normally affixed to the camera, surrounding the lens with an approximately pyramidal or conical shape, with the truncated point of the pyramid/cone being at the camera and the base of the pyramid/cone against the patient's skin. This approach is sometimes adequate for relatively flat or convex areas of skin, such as on a patient's back. The fixed focal point of prior art is fixed at the distance of the base of the pyramidal light shield. However, arrangement fails for some lesion locations, such as on the side of a patient's nose where the light baffle will not block the ambient or stray light.

Such art can include one or more of the following: Balch et al. J Clin Oncol 2001; 19:3635-3648; Folkman, J. (1971). New England Journal of Medicine, 285, 1182-1186; Folkman J, Klagsbrun M. In: Gottlieb A A, Plescia O J, Bishop D H L, eds. Fundamental Aspect of Neopla.sia. Berlin, Springer, 1975, 401-412; Ellis, et al. (2002). Oncology, 16, 14-22; Carmeliet, P., & Jain, R. K. (2000). Nature, 407, 249-257; Matsumoto et al. (2006). Performance characteristics of a new 3-dimensional continuous emission and spiral-transmission high sensitivity and high resolution PET-camera evaluated with the NEMA NU 2-2001 standard. Journal of Nuclear Medicine, 47, 83-90; Chatziioannou, A. F. (2005). Instrumentation for molecular imaging in preclinical research: Micro-PET and Micro-SPECT. Proceedings of the American Thoracic Society, 2, 533-536; Breslow, Annals of Surgery, vol. 172, no. 5, pp. 902-908, 1970; Heasley, S. Toda, and M. C. Mihm Jr., Surgical Clinics of North America, vol. 76, no. 6, pp. 1223-1255, 1996; Srivastava A, Hughes L E, Woodcock J P, Laidler P. Vascularity in cutaneous melanoma detected by Doppler sonography and histology: correlation with tumour behaviour. Br J Cancer. 1989 January; 59(1):89-91; Srivastava A, Laidler P, Hughes L E, Woodcock J, Shedden E J: Neovascularization in human cutaneous melanoma: A quantitative morphological and Doppler ultrasound study. Eur J Cancer Clin Oncol 1986, 22:1205-1209, which are hereby incorporated by reference in their entirety.

SUMMARY OF THE INVENTION

A need exists for improved systems and methods having desirable diagnostic features. Such desirable diagnostic features may include one or more of the following: is minimally invasive or non invasive; permits early stage disease detection; permits early body response to a new antigen; permits early body response to a foreign antigen, monitors disease development and progression; investigates the macro environment of the diseased cell and/or tissue as indication of presence of disease; is easy to use, low cost, provides a quick test to perform; can be performed by someone other than the physician; operates independent of skin color or ethnicity; provides immediate test results, provides consistency of results, works for a wide range of lesion types and body locations; is minimally dependent on human interpretation; is a simple test—minimal training necessary; provides automated or machine-assisted medical documentation, such as photographs or quantified test metrics; provides automated or machine-assisted electronic medical record keeping, such as machine readable codes on samples and files that directly tie to patient, doctor and date; operates independent of visual cues such as, color, shape and size; can identify melanoma in amelanotic skin lesion; and/or can identify melanoma in small lesions, less than 5 mm.

Methods, compositions and systems are provided for the imaging of lesions aligning tissue cavity/surfaces, including without limitation malignant lesions aligning tissue cavity/surfaces, e.g. cancers of the skin, mouth, cervix, bladder, etc. In some embodiments, the methods find use in the diagnosis of skin cancers including melanoma, skin basal cell carcinoma, etc., and non-cancerous skin diseases. The methods of the invention are useful in detection of melanoma not restricted by type, color, size, and body location or Breslow thickness and Clark level or the ABCDEF criteria.

In one or more embodiments of the invention, a detectably labeled biotag is applied to a tissue surface of an individual, e.g. skin, oral mucosal surface, bladder, cervix, lung, gastrointestinal and the like, generally in the region of a suspected lesion. The biotag selectively binds to a targeted binding partner present in lesions of interest. Alternatively the biotag is absorbed or metabolized or internalized or retained in other manner in reactive tissue. Application may be topical, for example application of a gel, liquid, etc. to the surface of the skin using a skin penetration agent or facilitator, or may be applied by sub- or intradermal injection, e.g. with one or an array of microneedles, to a depth of up to 1-5 mm or by electrical conductivity.

In some embodiments the tissue surface is preconditioned to increase delivery of the biotag through the surface, e.g. skin, etc. Preconditioning may include topical administration of a penetration vehicle in the absence of the biotag, where the vehicle optionally comprises a blocker agent, as described herein. The residual biotag is removed from the surface after a period of time sufficient for the biotag to penetrate the tissue surface.

A photograph of the tissue surface is taken using a camera and a light of the right (excitation) wavelengths that activates the biotag detectable label (in emission wavelengths) while taking a photograph capturing light of the same emission wavelength as the label. In some embodiments, the detectable label is a fluorescent label. When the lesion is diseased, e.g. cancerous; then the biotag will bind to the targeted binding partner, for example a cancer marker. Such binding can occur in the macroenvironment of the lesion, photographed. Optionally an image is taken to establish the base line status for the specific patient prior to application of the biotag.

The camera can also be used to take a picture of the same area using visible light. The two photos can be presented to a physician to analyze and compare. In some instances, the photos can be dynamically overlaid so that the physician can see where the retention of the biotag occurs on the tissue surface relative to features that are visually apparent, e.g. a mole, lesion, etc. Each photo can also be presented separately or combined as an overlay.

The invention provides a solution to significant prior problems with implementation. Prior art uses large, specialized expensive industrial cameras. Typical cameras used in the art cannot be practically or easily handheld. Variable focus at two different light wavelengths is a problem not resolved in the prior art. This invention overcomes numerous weaknesses in the prior art, in multiple embodiments.

Embodiments of the invention provide advantageous features and characteristics in the areas of the biotag, the camera, image identification, and/or automated image analysis, including methods, systems and/or devices of manufacture.

Aspects of various embodiments may include one or more of the following features, capabilities, or results, as are listed first in the table below, then explained in more detail.

TABLE 1

Use of a consumer, integrated camera as a starting point for the method of manufacturing the camera, for low cost, ability to be hand held, compactness, portability, and reliability. An industrial camera can also be used.
Use of the camera's built-in autofocus capabilities, and the autofocus software may be changed or updated.
Use of the camera's autofocus in the infrared range.
Use of the lens that comes with the camera, either integrated with the body or an interchangeable lens designed for use with the camera, preferably a macro-lens.
Two, three, or four light sources - one visible light for skin, one excitation light for cancer detection, one emission light for autofocus (option), and one for 3D and surface roughness image capture and analysis (option).
Dual, dynamically selectable light filters, one band pass for visible, one for IR detection. Optionally, a single filter with two pass-bands and one-stop band may be used.
Taking two photographs in two different wavelength bands using the same camera, optics, controls, and image storage.
Methods to align display and view the two above photographs.
Use of a biotag in conjunction with the other features of this invention.
Use of a multi-function fiducial.
Use of an eight-function fiducial (exposure/brightness, calibration, focus, patient orientation, patient id, linear metric, alignment of multiple images, number of mole on patient) optional information about the diagnostic procedure.
Use of machine-readable codes (1 D, 2D, text) on the fiducial, with machine printed on demand, pre-printed, hand-written areas, or a hybrid of these manufacturing attributes.
Use of both visible fiducial features and emission spectra features on the same or separate fiducial.
Changing the autofocus firmware on the camera to handle focusing in the infrared light band.
Removing the infrared blocking filter originally placed in the primary optical path in the camera during original manufacturing.
Removing the infrared blocking filter originally placed in the focusing optical path in the camera during original manufacturing.
Removing the RGB filter on top of the infrared filter optional. Removing the RGB filter will give better fluorescent sensitivity (about 15% more light) and higher pixel count in fluorescent but visible image will be black and white and not color.
Use of an engineered diffuser for one or two light sources.
Integrating all light sources and filters into a single, integrated camera that operates without an external computer or the need for external connectivity or power.

e.g. tumor vasculature, or on the cell surface, or within the diseased cells, and will be visible in the photograph. If the target marker is absent, the label will be substantially absent from the photograph (e.g., below background). In some embodiments, the biotag can bind to markers present in the macroenvironment proximal to the tumor cell even when a diseased cell is not specifically present in the area being This invention may include a consumer, prosumer, or "integrated" digital camera. This provides a large amount of value, functionality, and convenience, compared to large, expensive, non-portable custom-made medical cameras. Prior art has not been able to use an integrated camera in this application because of major deficiencies: the prior art camera can neither image nor auto-focus in the infrared light band. Also, the prior art camera does not include the necessary light sources nor the necessary filters. In addition, the prior art camera has no ability to overlay two different images.

This invention overcomes all of these deficiencies yet still maintains the fundamental benefits of a low-cost, compact, portable, handheld, reliable camera. Systems and methods provided herein may advantageously include removing one, two or three filters originally manufactured in the camera, modifying the auto-focus, adding light sources, adding dynamically selectable filters, and the use of complex fiducials to enable auto-exposure, auto-focus, and image alignment. When imaging light below 700 or 710 or 720 or 730 or 740 or 750 nm the filter many not need to be removed.

Autofocus is particularly important for two reasons. First, all stray light must be or is preferably blocked during exposure so that the maximum amount of light in the image is from the fluorescent biotag, along with information on the fiducial. This light blocking may be accomplished by having a light baffle that extends from the camera to patient's skin. Preferably, the end of the baffle that touches the patient is flexible to accommodate variations in the skin and the patient's anatomy. However, this flexibility and these variations mean that the distance from the area of interest to the camera lens is not constant. Traditional fixed focus cameras lack this flexibility, either compromising exposure or requiring a smaller numerical aperture, which lets in less light resulting in an inferior image or possibly blurring due to the long exposure then required. An alternative to a baffle is to place a cloth or other light blocking means over the patient and camera combination. This makes autofocus even more critical as it is now harder and less convenient to implement a fixed distance between the camera lens and the patient's area of interest, now hidden under the cloth. Another option is to turn off all room lights, which is even more impractical as well as having at least the same drawbacks as the cloth baffle.

Second, the patient's anatomy may present the area of interest in a recess, such at the side of the nose, making it very difficult or impossible to place the end of the camera baffle precisely at the right distance for a fixed focus camera.

Autofocus solves these practical problems of imaging a patient's skin in an environment free of stray light. However, implementing autofocus has not been achievable using prior art systems and techniques, which are overcome by this invention.

In another embodiment of this invention, features of the fiducials are used to enable automatic image analysis, processing, categorization, identification and filing of images.

Before the present compositions and methods are described in further detail, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, preferable methods and materials are now described. All publications, patents, and patent applications mentioned herein in this specification are incorporated herein by reference to disclose and describe the methods and/or materials in connection with which the publications are cited. Furthermore, all publications, patents, and patent applications mentioned in this specification are herein incorporated by reference to the same extent as if each individual publication, patent, or patent application was specifically and individually indicated to be incorporated by reference.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Definitions

We provide below the definition of terms as used herein.

AF—Autofocus.

Attachment to integrated imaging device—The attachment of key components, such as an excitation light source and/or filter, to the camera body may be permanent or temporary; may use an intermediate structure such as a plate or arm, clamp, lens, external battery pack or other external accessory to the camera, or other intermediate mechanical means. Suitable attachment is demonstrated by having a useable medical camera assembly, which may be hand-held. Key components of the camera may be supplied by and/or installed by the user, a technician, medical professional or other person including: battery or external battery pack, memory card, illumination modules, lens, filter, light hood or other modular, separable, standardized or interchangeable components. Components of the invention may be offered as a kit or may come from different suppliers.

Barcode—Machine-readable printing information, including 1D or 2D bar codes, matrix codes, OCR fonts, QR codes, etc.

Biotag—A specific binding partner to a targeted molecule of interest. Examples of biotags include, without limitation, peptide, peptidomimetic, peptoid, circular peptide, etc.; a nucleic acid such as RNA, DNA, aptamer, etc.; or other organic compound. One, or a cocktail of biotags of 2, 3 4, or more different moieties may be used in the methods of the invention for multiplex imaging. The biotag is of a molecular weight small enough to effectively cross the epidermal surface, e.g. usually less than 10,000 daltons, less than 5,000 daltons, less than 2,500 daltons, less than 1,000 daltons, which penetration may be facilitated by a penetration agent. The biotag generally comprises a detectable label.

Molecules suitable as binding partners to a biotag of the invention include, for example, cancer-associated markers present on cancer or pre-cancerous cells, or in the macroenvironment of cancerous or pre-cancerous cells, e.g. the vasculature at the site of the lesion. Specific markers of interest for this purpose include, without limitation, molecules associated with tumor vasculature, such as integrins, including integrin av, integrin a5, integrin β3, integrin β1, etc. Biotags suitable for detection of such integrins include peptides comprising an RGD motif or mimetics thereof, as known and used in the art. See, for example, Gaertner et al. (2012) Eur J Nucl Med Mol Imaging. 39 Suppl 1:S1 26-38; Danhier et al. (2012) Mo. Pharm. 9(11):2961-73, herein specifically incorporated by reference. Other biotags of interest include, without limitation, hormones, antigen binding fragments of antibodies, EGF, IGF, etc.

Tumor-associated antigens may include, without limitation, immunogenic sequences from MART-1, gp100 (pmel-17), tyrosinase, tyrosinase-related protein 1, tyrosinase-related protein 2, melanocyte-stimulating hormone receptor, MAGE1, MAGE2, MAGE3, MAGE12, BAGE, GAGE, NY-ESO-1, β-catenin, MUM-1, CDK4, caspase 8, KIA 0205, HLA-A2R1701, α-fetoprotein, telomerase catalytic protein, G-250, MUC-1, carcinoembryonic protein, p53, Her2/neu, triosephosphate isomerase, CDC-27, LDLR-FUT, telomerase reverse transcriptase, MUC18, ICAM-1, TNF α/β, plasminogen activator (uPA), Cathepsins (B, D, H, L), PSMA, HMB-45, S-100, Melan-A (A103), (T311), Mitf (D5), Glypican-3, GPC3, GPNMB, MIA (melanoma inhibitory activity), MCR-1, EGF, IGF, ARPC2, FN1, RGS1, SPP1, WNT2, PECAM-1, osteopontin, glucose, MMP-s (matrix metalloproteinase family members such as MMP-1. MMP-2, MMP-9, MMP-13, MT I-MMP and others) FDG (or other metabolites), VEGF, and the like, as known in the art.

Optically visible moieties for use as a detectable marker include fluorescent dyes, or visible-spectrum dyes, visible particles, and other visible labeling moieties. Fluorescent dyes such as fluorescein, coumarin, rhodamine, bodipy Texas red, and cyanine dyes, are useful when sufficient excitation energy can be provided to the site to be inspected visually. Endoscopic visualization procedures may be more compatible with the use of such labels. Acceptable dyes include FDA-approved food dyes and colors, which are non-toxic, although pharmaceutically acceptable dyes which have been approved for internal administration are preferred. Alternatively, visible particles, such as colloidal gold particles or latex particles, may be coupled to the biotag via a suitable chemical linker.

Fluorescent dyes of interest as a detectable label include, without limitation, fluorescein, rhodamine, indocyanine green (ICG), Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), the cyanine dyes, such as Cy3, Cy5, Cy 5.5, Alexa 542, Alexa 647, Alexa 680, Alexa 700, Bodipy 630/650, fluorescent particles, fluorescent semiconductor nanocrystals, and the like.

In some embodiments, the wavelength for emission from the label is in the range of the near infrared. Such labels include, without limitation, Alexa dyes such as Alexa 647, Alexa 680, Alexa 700 and Cyanine dyes such as Cy 5, Cy5.5. Cy7 Characteristics considered for label selection include its light absorption, and a minimization of autofluorescence from the body surface to be measured. The probe will respond to florescent illumination of a specific wavelength and will then emit light at a different wavelength.

Other dyes include, without limitation, any of the FDA approved dyes to use in food, e.g. FD&C Blue No. 1 E133, FD&C Blue No. E132, FD&C Green No. 3, Orange B(3), FD&C Red No. 3 E127, FD&C Red No. 40(3) E129, FD&C Yellow No. 5 E102, FD&C Yellow No. 6, D&C Black No. 2 &3, D&C Red No. 6, 7, 17, 21, 22, 27, 28, 30, 31, 33, 34, 36, 40, D&C Violet No. 2, etc.

In alternative embodiments the biotag is imaged by one or more modalities that may include, without limitation, optical coherence tomography, Raman spectroscopy, photo acoustic imaging, ultrasound imaging, endoscopy, and the like.

Calibrated Intensity—The effective intensity or brightness as viewed by a medical imaging device of an object or area of interest, such as a fiducial, can be known, either because the object has been manufactured or created to have a known and documented intensity or because the intensity has been measure or compared to a known standard.

Cavity—A cavity in a camera body may be used to accept a battery, storage card, wireless interface, communications cable, remote viewing screen, remote control accessory, mechanical mount or other accessory. The cavity may completely contain the item, as is common for batteries and storage cards, or it may partially contain the accessory, such as might be used for a wireless communication card with an antenna projecting from the body of the camera, or the cavity may simply be a recessed connector for the component. Some cameras come from the manufacturer with sufficient internal storage memory that a user-provided external storage card is not necessary.

Tissue/cavity surface—A layer of tissue covering the body surface or internal body cavities, such as the lining of the digestive tube, the mouth, pharynx, the terminal part of the rectum, the lining cells of all the glands which open into the digestive tube, including those of the liver and pancreas; the epithelium of the auditory tube and tympanic cavity; the trachea, bronchi, and air cells of the lungs; the urinary bladder and part of the urethra; and the follicle lining of the thyroid gland and thymus. In some instances, the surfaces come in contact with air, or fluids such as the skin, lung, colon, etc.

Diseased cell or tissue—A cell or tissue that is different or changed from the normal cell or tissue.

DSLR (digital single-lens reflex)—An SLR (single lens reflex camera) with an electronic image sensor.

Early stage disease—includes early stages of disease development prior to becoming recognizable or diagnosed using conventional methods. An example of early stage cancer is when a few cells are present before neoangiogenesis or vascularization, or a micro-foci. An example of non-cancer skin disease is the initial body response to a pathological signal or an antigen.

Cavity/tissue surface lining lesion. As used herein, the term refers to cancerous and pre, cancerous lesions of a cavity/surface lining. These could be ectodermal, endodermal or mesodermal tissues, particularly those tissues lining body cavities or surfaces in which a lesion is present within about 2.5 cm of an accessible surface, and which can be imaged by the methods of the invention. These tissues include, but not limited to the skin, the mucous membrane of the pharynx (including mouth and nose), the pharyngeal ducts, the larynx, the upper esophagus, the bronchial mucosa, the lining of the milk ducts, the small curvature of the stomach, the bile ducts of the liver, the gall bladder, the ducts of the pancreas, the urinary bladder, urethra and renal pelvis, the cervix uteri, and the lower part of the rectum.

The predominant cells of the ectodermis can be squamous epithelial cells, and certain cancers of interest can be squamous cell carcinomas (SCC), e.g. SCC of the lips, mouth, esophagus, urinary bladder, prostate, lung, vagina, and cervix. Other cancers of interest include, without limitation, basal cell carcinomas, melanomas, etc. For imaging lesions other than skin, e.g. bladder cancer, cervical cancer, etc., an endoscope may be preferable.

Effectively equivalent imaging sequence—This refers to taking a photograph or image that is functionally equivalent to another photograph or image taken under the discussed different condition. For example, a camera with an original internal infrared blocking filter performs a certain way, particularly with regard to the way various visible colors are rendered and the performance of the autofocus within the camera. The same camera with the original internal infrared filter removed and an external infrared filter added may then take substantially the same quality of photographs or images, including substantially the same autofocus performance. In this example the performance of the unmodified and modified camera would be effectively equivalent. The imaging sequence includes autofocus and auto-exposure, if the user has enabled these features. Functional equivalence in a medical context means the two comparative images can have the same or comparable medical value, but are not necessary visually identical.

Excitation light—Excitation light source, spectral band, or filter to pass excitation light must have some light overlapping with the excitation band of the subject of interest, such as the fluorescent portion of a biotag. However, the critical feature of excitation light or excitation light filters is that it has the lowest possible amount of light in the emission band of the subject of interest, which is our definition herein. Thus, the excitation light may not necessary have good spectral alignment with the excitation band of the subject of interest.

Structured light—Illumination of the object with a known pattern. For example illumination with multiple distinctive lines create line pattern on the object. Those lines can be used for 3D and roughness analysis of the object.

Exposure—Exposure is the process within a camera used to take a picture. The result of an exposure is one or digital images stored in the internal memory within the camera. The storage may be temporary; for example, the digital image data may be then transferred to a storage module, communicated via a communication port on the camera, or transmitted wirelessly via a wireless communication port on the camera.

Fluorescent imaging range—optimal imaging range for animals and humans is from 650 nm-850 nm.

Fluorescent marker or label—an entity that is able to emit fluorescence light that can be captured by a camera.

Industrial imaging system—This is an imaging system primarily designed for specialized, non-consumer applications, such as research and medical. The system is comprised of separate components, which may or may not be co-located in a single container, and may or not be considered portable. Components such as optics/sensor, illumination, image processing, memory, power supply, processor, and user-interface may be separated. Often, some of the components are off-the-shelf components, such as a processor, PC, or lens.

Integrated imaging system—This is a self-contained camera containing the following components: case, power-supply, lens, image sensor, image storage memory, user controls, user display, internal control electronics including stored instructions for an embedded processor, & internal image processing logic including stored instructions for an embedded processor. A consumer or professional digital single-lens reflex (DSLR) camera is one example of an integrated imaging system. The integrated imaging system may have interchangeable lenses, although this is not a requirement. The integrated imaging system may have an autofocus capability, such as a mirror-less contrast detection autofocus method or a phase detection method using a mirror and a separate sensor. The lens may have macro-focusing capability. The integrated imaging system may have removable image storage modules and/or have cable for communicating stored images, and/or a wireless communications port for communicating stored images. An integrated imaging system does not require connection to an external computer for operation, although such connection may be optional. An integrated imaging system is distinct from an industrial, medical or compound imaging system where required components and/or functionality are split between two or more physical enclosures and one of the enclosures is or contains a computer.

Internal image storage memory—This may be permanent image storage within the camera body or may be provided by a removable plug-in module in a cavity within the camera body provided for this purpose.

IR, or infrared light—can include near infrared wavelengths. Approximately the band from 650 nanometers to 4,000 nanometers.

Light baffle—A lightproof wall, material or container, which blocks stray or ambient light from entering the optics of the camera, predominantly between the entrance to the optical system and the patient. The baffle may be in the form of a truncated rectangular or conical pyramid. The baffle may consist entirely or in part of a flexible material, such as black cloth, and/or rigid material such as black paper, plastic, metal or other opaque, non-reflective material. Part or all of a baffle may comprise a cloth-like covering over the top of both the camera and patient, extending downward and around the patient and camera such that most or all of the ambient light is blocked from entering the optical system of the camera. In one embodiment the light baffle is a rigid, hollow, pyramidal tube attached temporarily or permanently at the narrow end to the camera with the wider end placed or pressed against the patient.

Linear distance reference on the patient's skin—This is a ruler, marks or other means, within the field of view, such that the whole or part of a photograph or image of the patient's skin may be dimensionally measured in linear units.

Macro environment—The cells or tissue in the proximity surrounding a diseased cell or lesion. Typically the macroenvironment, as used herein, refers to the extravascular space in the region of a lesion, including the outer walls of the vasculature.

Macro lens—Traditionally this referred to lens that imaged an object approximately as large or larger at the image place as the actual object. However, with the advent of modern high-density image sensors, we use the definition herein that a macro lens, macro focus, or macro imaging refers to the having a visible resulting image, when viewed at usable and appropriate resolution in either a hard copy or an electronically presented image where the viewed image is at least as large as the original image. For example, if imaging a patient mole whose actual diameter is one millimeter, a macro image could be any image of that mole displayed with a visible diameter of at least a one-millimeter.

Measuring a lesion—A lesion, such as a mole or cancer, is often measured for diagnostic and medical record keeping purposes. Such a measurement might be a diameter or circumference or thickness. Such measurement may be manual or automatic.

Microneedles (MN), as used herein, refers to one or more micro-projections (e.g., arranged in one or more rows, one or more columns, staggered rows and/or columns, or an array comprising a plurality of micro-projections), generally ranging from about 1 µm to about 5 µm or about 25 µm to about 2000 µm in length, which are attached to a base support. An array may comprise $10^2$, $10^3$, $10^4$, $10^5$ or more microneedles, and may range in area from about 0.1 cm$^2$ to about 100 cm$^2$. Application of MN arrays to biological membranes creates transport pathways of micron dimensions, which readily permit transport of macromolecules such as large polypeptides. In some embodiments of the invention, a microneedle array is formulated as a transdermal delivery patch. MN arrays can alternatively be integrated within an applicator device which, upon activation, can deliver the MN array into the skin surface, or the MN arrays can be applied to the skin and the device then activated to push the MN through the skin surface. MN can be used to deliver the biotag or the fiducial marking to the skin.

Various materials have been used for microneedles. In some embodiment, biodegradable materials into which the biotag can be incorporated are of interest. Such materials include various biodegradable or biocompatible polymers or cross-linked monomers, as known in the art. The biodegradable materials can be bioabsorbable. The biotags can be absorbed or incorporated to a target region as the microneedles biodegrade. The dose of biotag or fiducial to be delivered will vary, and may range from at least about 1 ng/microneedle array, at least about 10 ng, at least about 0.1 µg, at least about 1 µg, at least about 10 µg or more in a single array. MNs may be fabricated with a wide range of designs (different sizes and shapes) and different types (solid, hollow, sharp, or flat), and may be in-plane and/or out-of-plane.

Polymeric MNs can provide biocompatibility, biodegradability, strength, toughness, and optical clarity. To accurately produce the micro-scale dimensions of polymer MNs, a variety of mould-based techniques, such as casting, hot embossing, injection molding, and investment molding may be used, e.g. beveled-tip, chisel-tip, and tapered-cone polydimethylsiloxane (PDMS) molds. Polymeric materials of interest for fabrication include without limitation; poly (methylmetha-acrylate) (PMMA), poly-L-lactic acid (PLA), poly-glycolic acid (PGA), and poly-lactic-co-glycolic acid (PLGA), cyclic-olefin copolymer, poly (vinyl pyrrolidone), and sodium carboxymethyl cellulose. Sugars have also been used to fabricate the MNs, such as galactose, maltose, aliginate, chitosan, and dextrin. Materials may be cross-linked through ion exchange, photo-polymerization, and the like.

As an alternative to a biodegradable microneedle, a microneedle may be used which is a hollow needle having an exposed height of between about 0 and 1 mm and a total length of between about 0.3 mm to about 2.5 mm, usually between 30 to 34 gauge. Usually, the microneedle is a hollow needle having a length of less than about 2.5 mm. The biotags are delivered into the skin to a depth of at least about 0.3 mm and no more than about 2.5 mm by the microneedle. The biotags can be delivered through the hollow portion of the microneedle. The biotags can be stored and/or delivered via a channel in the microneedle. In some alternative embodiments, the microneedles can be coated with materials, such as biotags.

Near IR—Approximately the band from 650 to 1400 nanometers. Herein, the term "IR" or "infrared" generally refers to the near IR band or includes the near IR band, unless stated otherwise.

Medical Professional—Ideally a physician such as a dermatologist. However this term applies to any physician, healthcare provider, other medical personnel, or technician using this invention. The medical professional can include any individual with training or knowledge of use of the systems and methods described herein. In some embodiments, it can include the patient.

Removable optical filter—The filter may be completely removed or may be repositioned so that it is no longer in the optical path of the camera. The movement of the filter may be completely manual, or may be assisted by a powered mechanism whose operation is controlled by a user; or may be completely automated. More than one filter may be involved. For example, one or more filters may be on a slide, where one filter is selected by moving the slide. One or more filters may be in a rotating carousel. One or more filters may rotate, or flip on a hinge out of the optical path. A suitable hinge design is similar to the design on popular flip-up sunglasses.

SLR—Single lens reflex camera.

Transmit or block wavelengths of light—An ideal filter may be characterized by passing 100% of light within a pass band and passing 0% of light outside that pass band. Such an idealized filter has an associated spectral curve in the shape of a rectangle with at least one vertical edge. However, available filters, as one trained in the art appreciates, have sloped sides in their spectral curve. In addition, the light passed in the pass band is often slightly less than 100% and the amount of light passed outside the pass band is often more than 0%. This means that there is a range of wavelengths of light in which the amount of light passed by the filter varies, perhaps monotically or perhaps non-monotically, from within the pass band to outside the pass band. Thus, there is no exact cutoff frequency defining at least one side of the pass band. Filters may also be low pass or high pass. By convention, depending on the type of filter and the application, the stated pass band threshold might be at the wavelength where 50% of the light passes through the filter, or might be determined by some other metric. When we refer herein to a spectra, pass band, range, excitation band, emission band, transmission or blockage of light, or other reference to a range of light wavelengths, we are using the accepted terms of the art to describe the band including the understanding that passing and blocking light may be less than 100% or more than 0% respectively.

Visible light—Approximately in the band from 400 to 700 nanometers. Within the light band from 650 to 1400 nanometers—The ideal band for focus is at the same infrared wavelength as the peak emission wavelength of a fluorescent emission from the biotag on the patient. However, there is typically considerable latitude in exact range of wavelengths usable for autofocus. The autofocus does not necessary have to focus on all wavelengths or any wavelengths from 650 to 1400 nm, but rather has to focus on the emission wavelengths for the biotags in use. In one embodiment using Cy5.5 as the fluorescent compound this range is approximately 690 to 750 nm. In another embodiment using ICG as the fluorescent compound this range is approximately 815 to 915 nm.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the claimed invention are set forth with particularity in the appended claims. A better understanding of the features and advantages will be obtained by reference to the following detailed description that sets forth illustrative embodiments, and the accompanying drawings or figures (also "FIG." or "FIGs." herein) of which:

FIG. 3a shows a cutaway view of one embodiment of the camera.

FIG. 3b shows an isometric view of the camera from the back.

FIGS. 8a and 8b show a benign mole topically treated with a biotag in visible light and IR light, respectively.

FIGS. 9a and 9b show a recurring melanoma mole topically treated with a biotag in visible light and IR light, respectively.

DETAILED DESCRIPTION

Figure 1A:
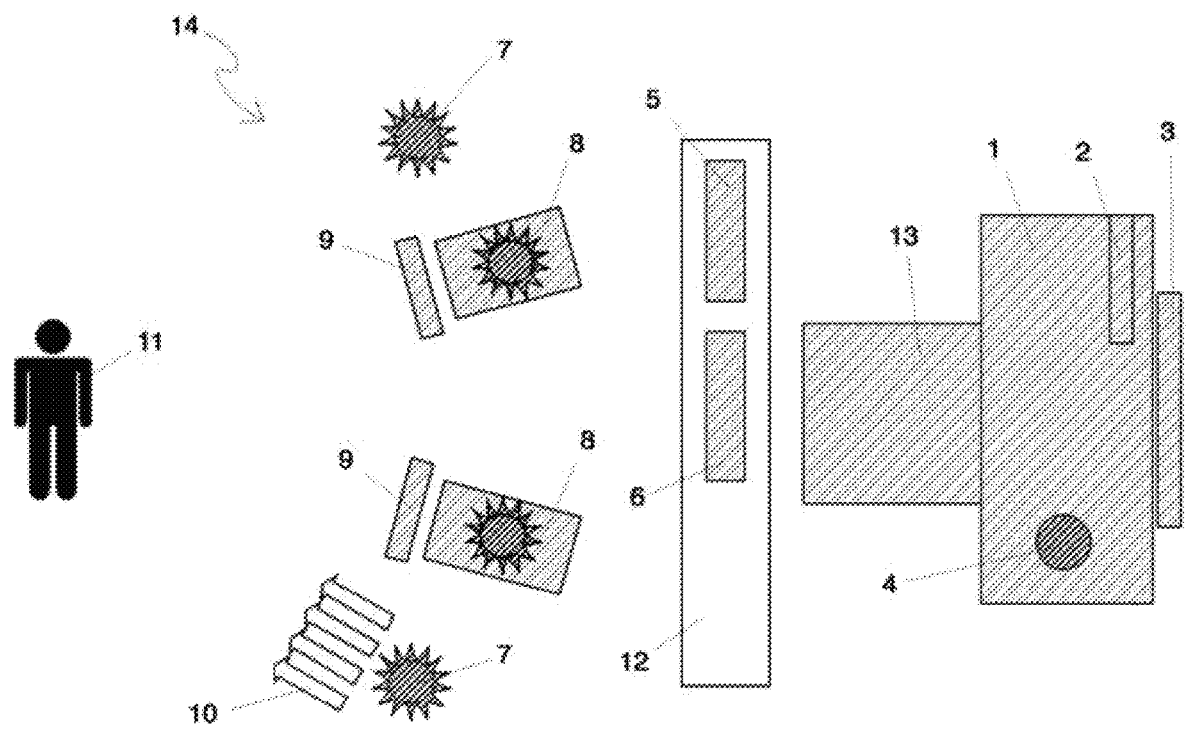
FIG. 1a shows a block diagram of a camera.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

In one aspect, systems, compositions and methods are provided for imaging of cavity and/or tissue lesions. Various aspects described herein can be applied to any of the particular applications set forth below, alone or in combination, or for any other types of imaging systems. The embodiments described herein may be applied as a stand-alone system or method, or as part of an integrated medical diagnostic and/or treatment system. It shall be understood that different aspects can be appreciated individually, collectively, or in combination with each other.

Methods of Analysis

Systems and methods may be provided to image and/or analyze a target region. In some embodiments, the target region may include a cavity/tissue surface. The cavity/tissue surface that is to be analyzed can be identified, e.g. by the presence of a suspected lesion. In some embodiments a target area may be the surface of cavity/tissue compartments where there is a suspicion of cancer cancerous or pre-cancerous lesion, which may be referred to as an area of interest or diagnostic area of interest. Surfaces include skin, cervix, oral mucosal surfaces, bladder, and the like. In some embodiments the surface is skin.

A suspected lesion can be less than about 0.5, 1, 2, 3, 4, 5, 6, 7, 8, 9, 10, 11, 12, 13, 14, 15, 16, 17, 18, 19, or 20 mm in diameter (or any other dimension such as radius, length, width, height, perimeter, or circumference). The suspected lesion may be above 20 mm in diameter. A suspicious lesion may be asymmetric or symmetric. A suspicious lesion may have regular or irregular borders. The lesion may or may not contain excess pigment or melanin. The lesion may or may not contain more than 1 color. The lesion may or may not be evolving. The lesion may or may not induce a noticeable sensation to the patient. The cavity/tissue surface may be cleaned with water, alcohol, and/or a surfactant prior to the assay, or by other means as typical in a medical professional's practice.

The cavity/tissue surface is optionally preconditioned to increase delivery of the biotag through the surface. For preconditioning, a penetration enhancer can be applied to the cavity/tissue surface prior to contacting the surface with the biotag. Penetration enhancers can include sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and/or terpenes. DMSO is of particular interest. The concentration of penetration enhancer may range from 10-90% or 10, 15, 20, 25, 30, 35, 40, 45, 50, 55, 60, 65, 70, 75, 80, 85, 90% or 10-15, 15-20, 20-25, 25-30, 30-35, 35-40, 40-45, 45-50, 50-55, 55-60, 60-65, 65-70, 70-75, 75-80, 80-85, or 85-90% or 10-20, 20-30, 30-40, 40-50, 50-60, 60-70, 70-80, 80-90%. In some instances, if a penetration enhancer is DMSO, a preferable range of DMSO concentration may be between 40-70%.

Optionally, as an additional preconditioning step, or in combination with preconditioning using a penetration enhancer, a blocker can be added to the vehicle. The blocker may be a protein not associated with the lesion of interest, e.g. albumin, casein, etc. The blocker concentration may range from 0.01 to 10%, or 0.01-0.1, 0.1-0.2, 0.2-0.3, 0.3-0.4, 0.4-0.5, 0.5-0.6, 0.6-0.7, 0.7-0.8, 0.8-0.9, 0.9-1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10%. A preferable blocker concentration can be between 0.2%-2%.

In some embodiments the invention includes a method of enhancing the transfer of an agent across intact skin, the method comprising preconditioning the skin by topically applying an effective dose of a penetration enhancer in the absence of the agent, for a period of time (e.g., from 5 to 30 minutes); and topically applying the agent in a vehicle comprising a penetration enhancer, wherein transfer of the agent across intact skin is increased relative to transfer in the absence of preconditioning.

In some embodiments, the biotag is next applied to the cavity/tissue surface. The biotag is generally formulated in a physiologically acceptable vehicle, which optionally comprises a penetration enhancer as described above. The biotag can be applied topically to the region of interest, or by subdermal injection with a microneedle to the area of interest or diagnostic area of interest. In some embodiments, penetration of the biotag is within about 2 cm of the surface. The biotag may penetrate about or less than 0.1 cm, 0.3 cm, 0.5 cm, 0.7 cm, 1.0 cm, 1.3 cm, 1.5 cm, or 2.0 cm. Where administration is by subdermal injection it will not be necessary to include a penetration enhancer in the formulation. In the methods of the invention the biotag is not injected into the bloodstream. For example this approach being less invasive is also less subject to side effects and does not require a sterile needle. Topical application provides a number of benefits, in being non-invasive, not requiring a sterile needle, and it is also easier for the medical professional. Methods of application includes the use of micro-needles, nano-needles, active patches and passive patches. Topical application includes the use of a gel, such as a gel that needs to be activated, either chemically or mechanically, from a storage state to a usable state.

The biotag formulation can comprise a solvent, and optionally blocker, skin penetrator and/or an enhancer, ion-pairing agent, co-solvent and/or humectants and/or thickeners, alone or in various combinations. The solvent functions as the carrier for the biotag. The skin penetrator facilitates transdermal penetration. The enhancer reduces the background noise by inducing efficient stratum cornea transfer. The blocker blocks exposed epitopes in the skin and prevents or reduces non-specific binding of the biotag to these epitopes. The formulation may be a liquid or gel, e.g. a thickener may be included to generate a gel-like formulation or in a formulation composed of micelles or reverse micelles in a liquid or spray dispenser. With a liquid formulation, a barrier is added in some embodiments to prevent the liquid from rolling off the skin. This barrier can be a gel-like substance that generates a surface tension for an appropriate quantity of the transdermal penetration combination, or a mechanical barrier, such as a polymer.

Alternatively the biotag can be adhered to a membrane and dried, where a solvent, including for example a penetration enhancer, is used to wet the membrane immediately prior to contact with the cavity/tissue surface.

Desirably the formulation provides for a rapid release of the biotag agent from the vehicle to the cavity/tissue surface; the biotag could be rapidly transported across the cavity/tissue surface to produce a low background image; residual vehicle components preferably should not dissociate from the biotag after transport, so not to interfere with biotag binding; be non-toxic or sensitizing; be acceptable to FDA and EMA regulatory reviewers; optionally contain a viscosity building agent so the formulation stays in place until the vehicle penetrates the surface; and/or be easy to remove the residue from the surface. A rapid transport may be less than about 5, 10, or 15 minutes.

Solvents or cosolvents include water, saline, DMSO, ethanol, proplyene glycol, PEG 300, N-methyl pyrollidone, isopropyl myrstate, labrafil, labrasol, gelucires, surfactants, dodecyl pyridinium chloride, poloxamer, sorbitol, oils, glycerin, azone; diethylene glycol monoethyl ether; nonoxynol-9; NMP; cyclodextrins; surfactants (such as tween 80 and cremophor); vitamin E TPGS; and the like as known in the art.

Ion pairing agents include ethanolamine, triethanolamine and dodecyl pyridinium chloride; oleic acid and sodium lauryl sulfate; and many others.

Co-solvent and humectants include propylene glycol or isopropyl myrstate.

Thickeners include hydroxyethyl cellulose, carbomer or starch.

The formulation may be provided as a lyophilized substance in single or multiple use units. It may be reconstituted by a pharmacist or the medical professional before use. Alternatively it is provided in a stable formulation where no reconstitution is required and may be used directly by the medical provider.

The dose of the biotag may be 1 fg-1 g, 1 fg-1 pg, 1 pg-1 ng 1 pg-1 microg, 1 microg-1 mg, 1 mg-1 g, 1-10, 10-20, 20-30, 30-40, 40-50, 50-60, 60-70, 70-80, 80-90, 90-100, 100-150, 150-200, 200-250, 250-300, 300-350, 350-400, 400-450, 450, 500, 500-550, 550-600, 600-650, 650-700, 700-750, 750-800-800-850, 850-900, 900-1000 fg, 1-10, 10-20, 20-30, 30-40, 40-50, 50-60, 60-70, 70-80, 80-90, 90-100 pg, 1-10, 10-20, 20-30, 30-40, 40-50, 50-60, 60-70, 70-80, 80-90, 90-100, 100-150, 150-200, 200-250, 250-300, 300-350, 350-400, 400-450, 450, 500, 500-550, 550-600, 600-650, 650-700, 700-750, 750-800-800-850, 850-900, 900-1000 ng, 1-10, 10-20, 20-30, 30-40, 40-50, 50-60, 60-70, 70-80, 80-90, 90-100, 100-150, 150-200, 200-250, 250-300, 300-350, 350-400, 400-450, 450, 500, 500-550, 550-600, 600-650, 650-700, 700-750, 750-800-800-850, 850-900, 900-1000 microg, 1-10, 10-20, 20-30, 30-40, 40-50, 50-60, 60-70, 70-80, 80-90, 90-100, 100-150, 150-200, 200-250, 250-300, 300-350, 350-400, 400-450, 450, 500, 500-550, 550-600, 600-650, 650-700, 700-750, 750-800-800-850, 850-900, 900-1000 mg, 1-10, 10-20, 20-30, 30-40, 40-50, 50-60, 60-70, 70-80, 80-90, 90-100, 100-150, 150-200, 200-250, 250-300, 300-350, 350-400, 400-450, 450, 500, 500-550, 550-600, 600-650, 650-700, 700-750, 750-800-800-850, 850-900, 900-1000 g. The preferred amount biotag in one embodiment is between 1 fg-0.1 microg. The units may be read so that fg is femtograms; pg is picograms; ng is nanograms; microg is micrograms; mg is milligrams; g is grams.

A preferable volume of biotag applied to the cavity/tissue surface is between 50 to 150 microliter per square centimeter. Depending on the application and the embodiment, the biotag can be applied in a volume of 50, 100, 150, 200, 250, 300, 350, 400, 450, 500, 550, 600, 650, 700, 750, 800, 850, 900, 950, or 1000 microliters.

Depending on the application and in one embodiment, the biotag formulation may be 10-90% or 10, 15, 20, 25, 30, 35, 40, 45, 50, 55, 60, 65, 70, 75, 80, 85, 90% or 10-15, 15-20, 20-25, 25-30, 30-35, 35-40, 40-45, 45-50, 50-55, 55-60, 60-65, 65-70, 70-75, 75-80, 80-85, 85-90% or 10-20, 20-30, 30-40, 40-50, 50-60, 60-70, 70-80, or 80-90% DMSO.

The biotag interacts with the tissue and binds to the appropriate binding partners, a process that typically takes several minutes. The excess, unbound biotag material is then removed. In some examples removal may occur via washing or wiping with water or saline solution, with or without a detergent. Depending on the application and the embodiment, excess (non-bound or non-retained) biotag can be removed after 1, 2, 3, 4, 5, 6, 7, 8, 9, 10, 11, 12, 13, 14, 15, 16, 17, 18, 18, 20 minutes or within 20-25, 25-30, 30-35, 35-40, 40-45, 50-55, 55-60 minutes, or within 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24 hours or within 1-2 days. A preferable time of biotag application is between 2 to 15 minutes and less than 2 hours. Retention of the biotag in the cavity/tissue compartment occurs when the appropriate binding partner is found in the lesion macroenvironment.

In one embodiment, prior to imaging the area of interest, calibration markers in the form of fiducials can be applied proximal to the lesion in the area of interest. Fiducials are placed on the patient or fixed to the imaging device. The fiducials can be removably provided on the patient, drawn on the patient, affixed (removably or permanently) to the imaging device or provided separately from the imaging device. Depending on the application, images may be acquired prior to application of the biotag as well as after application. Images may be acquired using a camera, or any of the devices, systems and methods described within this specification.

In some embodiments, a camera takes two images of the area of interest. One image (color or gray scale) can use visible light and the second image can use light in the emission spectra of the biotag. The emission light may be activated by light from the camera in the activation band of the biotag.

Images are typically transferred out of the camera for further medical analysis. Such analysis can include comparing statistical features calculated on both image, merged or overlaid image composed of both the visible light image and the emission light image of the area of interest. In an alternative embodiment, the pair of images is presented as a pair, although the former presentation is preferred. Such statistical features can include dimensions, brightness, intensity, contrast, color, mapped 3D features or texture, or any other features discernible from images.

The images are analyzed to identify the intensity of the reporter tag retention of the imaging agent in the surrounding tissue and the pattern of its retention in the tissue of interest. The image intensity is calibrated to the intensity of the calibration tags.

In some embodiments the calibration tag contains a unique barcode or other identifier for identification of the lesion imaged. (Barcode generally refers to information which is unique for a specific tag, e.g.: linear barcode, 2D metric barcode) The calibration tag can include a visual identifier.

Figure 2A:
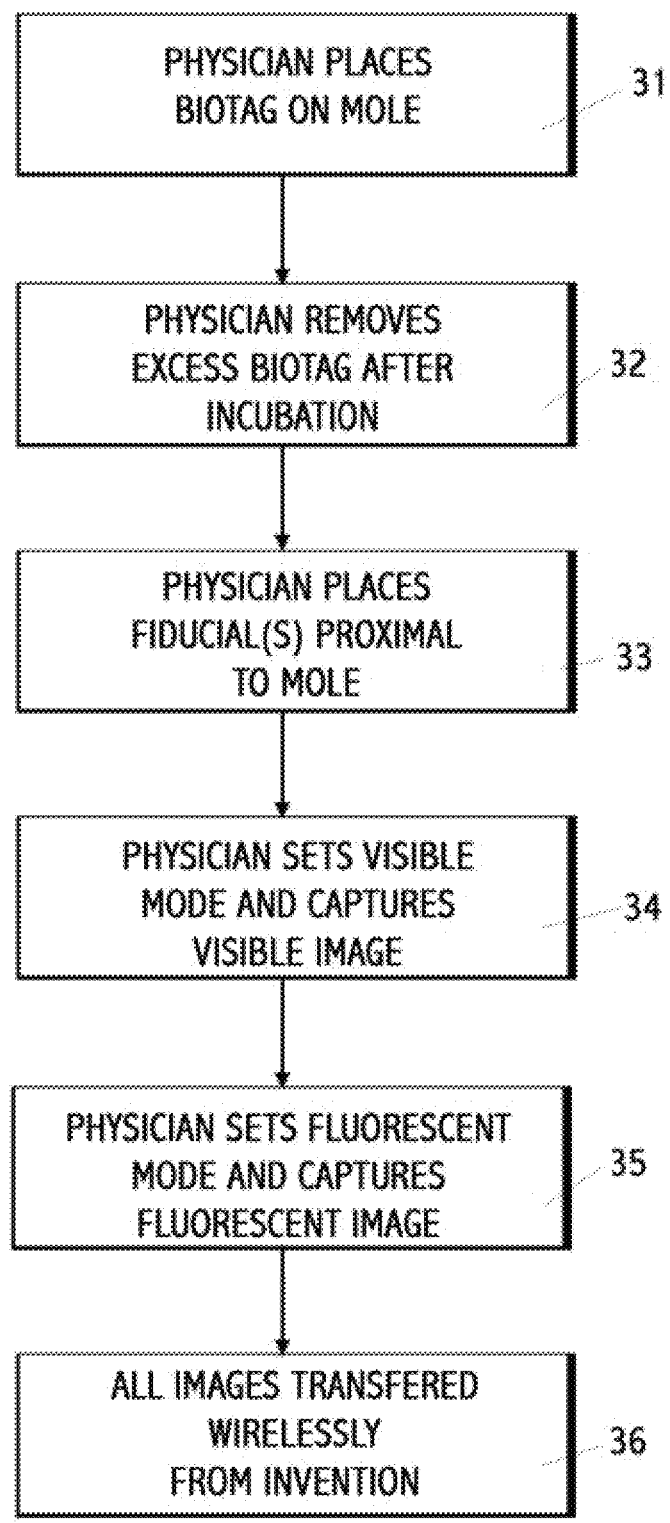
FIG. 2a shows one embodiment of a method of diagnosis.
Figure 2B:
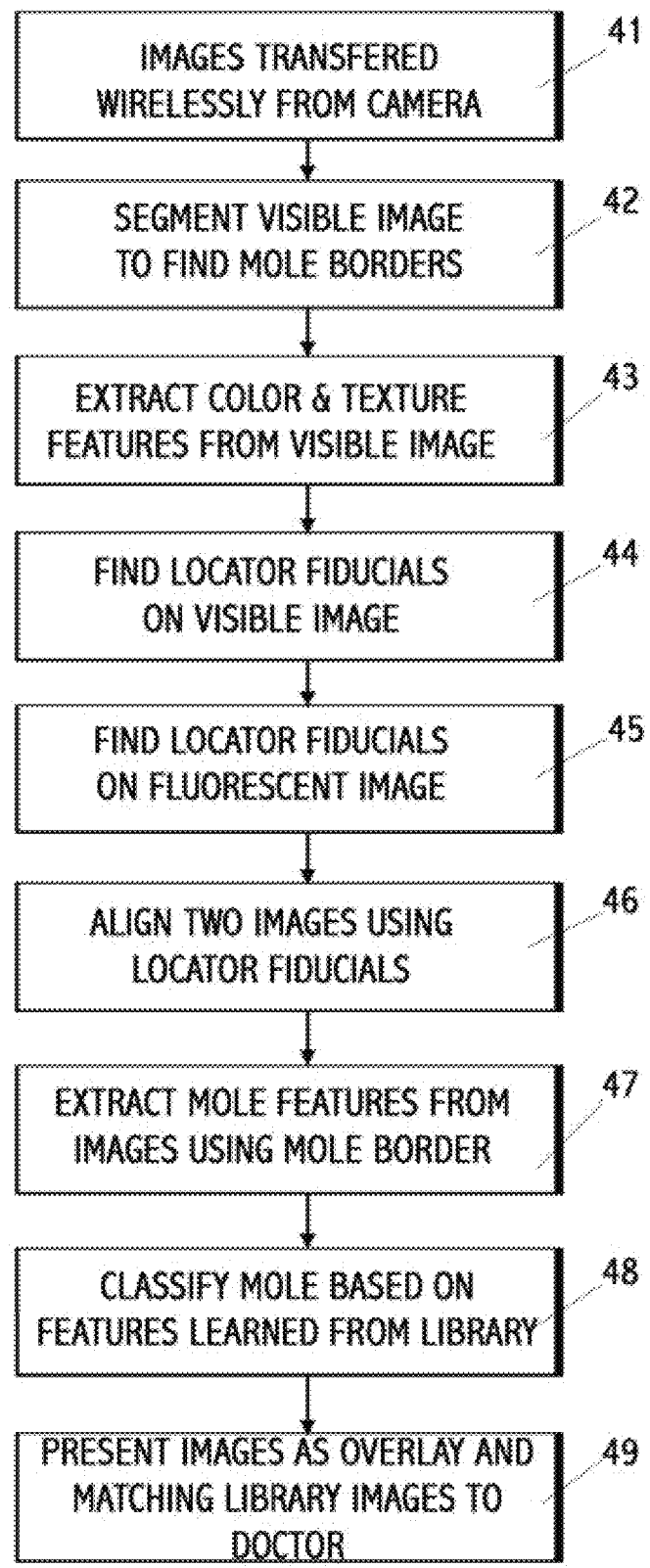
FIG. 2b shows one embodiment of a method for image transfer and mole classification.

The analysis output can be stratified into the classifications reflecting the probability of the lesion being a tumor. FIGS. 2a and 2b provide examples of methods of analysis.

Tumor Detection

In some embodiments, diagnostic methods are based on imaging of an externally applied biotag that specifically interacts with a cancer-associated entity of interest, and thus which distinguishes between pathological and non-pathological lesions on a surface of the body. Markers of interest include markers expressed on neoplastic cells, markers selectively expressed on neoplastic cells or their surrounding of the microenvironment, makers associated with tissue remodeling, markers on immune cells recruited to the skin under investigation following the application of an entity that may recruit the response, markers expressed on cells associated with tumor angiogenesis; markers secreted by neoplastic cells; and the like, particularly cell surface or secreted markers. Optionally the marker is compared to a negative and/or positive control, e.g. a fluorophore in the absence of a binding probe as a negative control; and the like. Alternatively, optional instructions depicting positive and negative images may be included in kits of the invention.

Topical Application

In some embodiments of the invention, an optimized or improved procedure for image acquisition with minimal or reduced background noise utilizes the following process for biotag application. The tissue cavity surface can be first cleaned with a cleaning solution, comprising typically alcohol, or surfactant, or saline or water or some combination of these. The lesion is contained using a barrier, or alternatively the biotag is applied in a gel formulation. Examples of such barriers include petroleum jelly, a polymer applied directly to the skin, or another barrier means. Next, the stratum cornea is prepared. A preconditioning formulation of penetration enhancer with or without blocker is topically applied. After a short time for incubation of the preconditioning formulation, the biotag formulation is applied to the cavity/tissue surface. After a time for incubation of the biotag formulation, the excess can be washed away using saline or water with or without a detergent or other surfactant. The time for incubation can be a predetermined amount of time, such as time quantities described elsewhere herein. The time for incubation can be flexible and dependent on one or more indicators.

Application may alternatively be via intradermal or subdermal injection, instead of topical. Application may alternatively be by spray. Methods of application also include the use of micro-needles, nano-needles, active patches and passive patches Camera An imaging device may be used to image a target area of interest. The imaging device may be a camera having one or more components, characteristics, or features described herein. FIG. 1a, FIG. 1b, FIG. 3a, and FIG. 3b provide examples of imaging devices that may be used in accordance with embodiments of the invention. Preferably, the camera imaging the area of interest has autofocus and is able to focus on the lesion itself. Such a system might be theoretically possible if the lesion emits fluorescently from the biotag. However, if there are no cancerous cells in the lesion then the biotag will be missing and there will be no light source on which the camera can focus. Therefore, to handle the case of non-cancerous lesions, this invention uses the addition of a novel fiducial. The fiducial comprises a fluorescent marker or tag which comprises either the same fluorescent compound as the fluorescent marker present on the biotag, or comprises a compound that emits light in a compatible spectra as the biotag (for example FD&C Green No. 3) so that it can be detected by the camera optics and used as a target for autofocus. Compatible spectra include, for example, a spectrum that comprises excitation light in the spectra of the excitation of the biotag, and light emission of the fiducial comprises a spectral emission within the spectrum of the biotag emission. In some cases, common food coloring is be used as the fluorescent compound in the fiducial. The fiducial can be applied directly to the tissue/cavity surface or on a medium that is then applied to the surface, for example a sticker or transferred from a medium to the skin, for example a temporary or permanent tattoo.

This method of this invention can include both the use of autofocus in the camera and the use of a fluorescent fiducial. It can also include the use of autofocus independently, the use of a fluorescent fiducial independently, or neither of these features.

In a preferable embodiment, a user input on the integrated imaging device changes the autofocus from visible light to infrared light. This is required or preferable when the autofocus is based on phase detection due to the different width of the phase lines when properly focused in IR as compared to visible light. For contrast-based autofocus, no change in the algorithm or constants is needed and thus no user input on the camera is needed. Alternatively, the means to select visible or IR autofocus is determined automatically from which illuminator is on, respectively. One means, the preferred embodiment, uses the mode dial or push button on the camera to for this selection. Either a "custom mode" provided on the dial is programmed for this purpose, or one of the other modes, such as "portrait," or "night" mode is taken over for this purpose. Touch-screen based camera control systems are ideally extensible to provide specifically for this selection explicitly. An integrated imaging device can permit an autofocus change between different spectra of electromagnetic radiation, such as visible light and infrared light. Such autofocus can occur manually with user input, or automatically without requiring user input. Such autofocus may occur with aid of a processor.

In some embodiments fiducials are not used, or they are not suitable for autofocus. This may be remedied by adding an additional light source that emits light in comparable spectra to the emission wavelengths of the biotag, then using the auto-focus to focus on the subject using this light. In one embodiment, this light source is provided integral to the invention, using narrow-band LEDs or LEDs with a spectral filter. After the auto-focus completes, this light source is turned off and immediately the excitation light source is turned on, and the picture is taken. Any light source known in the art may be utilized, which may include light emitting diodes (LEDs), electron stimulated light sources, incandescent light sources, electroluminescent light sources, gas discharge lamps, or high-intensity gas discharge lamps. Light sources may be electrically powered and/or may utilize chemical or biological luminescence.

There is nothing in this invention that precludes the use of industrial cameras or other imaging devices or technologies. As an example, an integrated imaging system permits the addition of user-provided software. A first example is a camera running the Android OS with a USB interface. A user-provide app, running on the camera, performs the methods described herein; while the USB interface provides an interface to functionality not provided originally in the camera, such as turning on and off illumination, moving filters, and the like. The camera may optionally include a local memory and/or processor. The local memory may store non-transitory computer readable media comprising code, logic, instructions to perform one or more steps. The processor may be capable of performing one or more steps, optionally in accordance with the non-transitory computer readable media. A second example of an alternative imaging system comprises off-the-shelf optics and an imager, with a single-board computer providing a processor and memory, or a memory interface, for implementing the methods described herein. As a third example, a portable electronic device such as a tablet or smart phone provides the platform for an app, memory, and the user interface of this invention. The portable electronic devices uses a built-in interface such as USB or Bluetooth to interface to required functionality not initially included in the portable electronic device. The camera may include one or more of the functionalities on-board or may communicate with one or more external devices that provide one or more of the functionalities described herein. The camera may communicate with an external device via a wired or wireless communication. The camera may communicate directly with an external device or devices, or may communicate with the external device or devices over a network, such as a local area network (LAN), wide area network (WAN) such as the Internet, telecommunications network, or any other network. Such cameras may also find use in the methods of the invention as an endoscope, i.e. a general industrial camera with fiber optics to transfer the image, as is known in the art.

Operation of the camera includes various degrees of manual operation and automatic operation, depending on embodiment. In a more manual embodiment, the two photographs in IR light and visible light are taken separately. The filters in the optical path are moved manually between exposures. The shutter release button is pressed once for each image to be acquired. In a more automatic embodiment, "one button" operation takes both images, automatically changing the filters and camera modes between the two exposures.

This second, "one button" embodiment can be implemented within the firmware of the integrated imaging device, which is updated for this purpose from the firmware provide by the manufacturer of the integrated imaging device. Alternatively, a separate controller can be used, which is integrated into the camera of this invention, but is not internal to the integrated imaging device. In the latter case, a microprocessor and control logic comprise a typical implementation. Ideally, the "one button" is the existing shutter release on the integrated imaging device. However, it may also be a separate button, which is an input to the separate controller. To move the filters, a simple motor can be used with a slide or hinges. In further alternative embodiments, the separate controller can be external to the camera.

Imaging

In accordance with an embodiment, the imaging process may take both a visible light (e.g., white light) color image and also an image using light in the emission spectra. These two images are taken in either order. The emission spectra image typically uses as light sources only the emitted light from the detectable label components of the biotag and/or the fiducials. These light sources are activated by light in the activation spectra of the fluorescent components, where the activation light comes from the camera. However, an emission spectra image may alternatively be acquired of light emitted in the range of a fluorescent label.

Generally, when the two images are analyzed together for a medical purpose, the visible light image shows what a person sees, such as a mole, and the emission spectra image, because of the biotag and the other elements of this invention, shows the cancerous cells.

Generally when triple images are analyzed the structure illumination image is used to analyze the roughness of the mole and to segment the hair that obscures the mole. Hair might be filtered or subtracted from the image based on the hair segmentation.

An image of the area of interest in the emission spectra is to be taken prior to the application of the biotag for background subtraction proposes, in some embodiments.

In accordance with embodiments of the invention, multiple images may be captured. The multiple images may be captured under different light source spectra or wavelengths. Multi-wavelength images may be captured. For example one or more white light source or fluorescence light source may be used. One or more images may include analysis of features shown in the images. The images may be captured from the same angle or varying angles. One, two, three, four or more images may be captured. The images may be compared, contrasted, and/or overlaid.

Image processing and analysis may be manual or automatic, depending on embodiment. Maximizing the processing performed automatically is the preferred embodiment. Computerized image processing may be performed in the camera, using its embedded processor, or on a computer, tablet, smart phone or other electronic computational device. The steps of image processing can be split among multiple devices.

The embodiment of using white light is not a requirement for this invention. The dual wavelength images have substantial diagnostic advantage. However, for the simplest and lowest cost implementation, such as might be used for home use, or in remote clinics only single wavelength range images, such as the fluorescent image is used. For example, seeing and identifying the mole border is generally practical with only the fluorescent image. Medical diagnoses may be incomplete in some embodiments, but any visible biotag fluorescence in the image is a strong indication that additional medical diagnosis and treatment is necessary.

Automated Analysis

Steps of automated analysis include one or more of the following.

First, the lesion is automatically or manually outlined in the white light image. The fiducials can be identified in this image. The white light image is then overlaid on the fluorescent image using the elements of the fiducial for this purpose. The lesion circumference is identified in the fluorescent image. This circumference is to be measured, in one embodiment, using the measurement elements provided by the fiducial. The measurement element provided by the fiducial may be used for measurement calibration, and measurement may occurred automatically with aid of a processor. Fluorescent intensity is compared in the fluorescent image in the mole and around the lesion. The intensity is calculated compared to the fluorescence in the calibrated portion in the fiducials. The intensity can be calculated with aid of a processor.

Fluorescence is also calculated in the skin around the lesion and in the lesion and compared to fluorescence image taken before the biotag is applied, if an image of the area of interest was taken prior to application of the biotag.

Additional features are extracted using image analysis algorithms to identify features that distinguish and stratify moles according to level of increasing malignancy. A processor may perform one or more steps or calculations dictated by the analysis algorithms.

Figure 4:
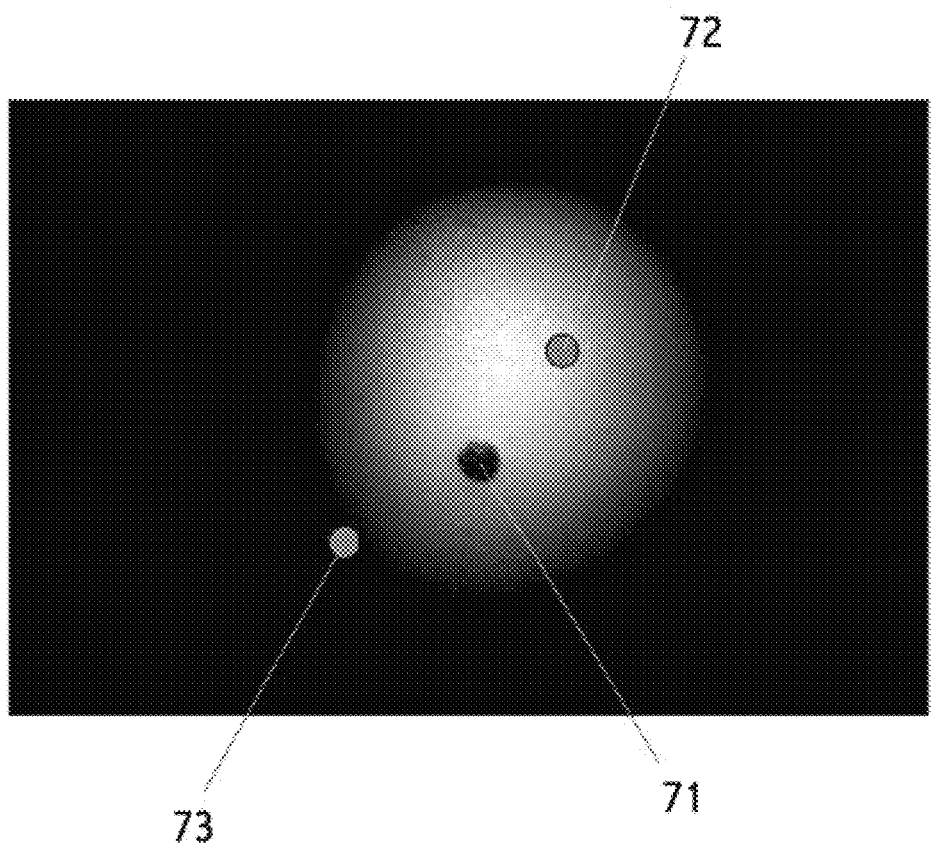
FIG. 4 shows a black and white photographic image from the invention showing a mole and two fiducials using white light.

FIG. 4 provides an example of an image useful for or generated during automated analysis.

Analysis Presentation

Depending on embodiment, results of the analysis may be presented graphically in 2-D or 3-D figure. Results may be presented in black & white or color. The location of the lesion analyzed can be placed and located on graph. A database including a collection of lesion analyzed may be included in the representation. Images of lesion in the database most similar to the patient's lesion may be selected from the database and presented. The database may be searched with aid of a processor for the most similar images.

Depending on embodiment, a score may also be calculated to represent the likelihood of a mole having a specific characteristics analyzed by the software or a combined score of likelihood of a mole being melanoma or a recommendation for a biopsy or a recommendation for additional evaluation. The score may be a numerical score along a scale that may provide likelihood of the detection of cancerous tissue. The score may be used to recommend one or more medical action, such as biopsy or additional evaluation. Additional factors, such as specific image characteristics (e.g., dimensions, brightness, contrast, intensity, texture, color) can be used to provide qualitative evaluations or recommendations for medical actions.

Depending on embodiment, measurements, metrics and scores may be presented numerically or graphically.

Depending on embodiment, the visible light image and the emission spectra image may be presented interactively by the use of an operable slider that shows 100% of the visible light image at one end and 100% of the emission spectra image at the other end, with variable portions of each image overlaid for intermediate slider positions.

Depending on embodiment, the emission spectra image may be presented in a contrasting color overlaid with the visible light image. For example, fluorescence may show as bright green.

3-D

Figure 12:
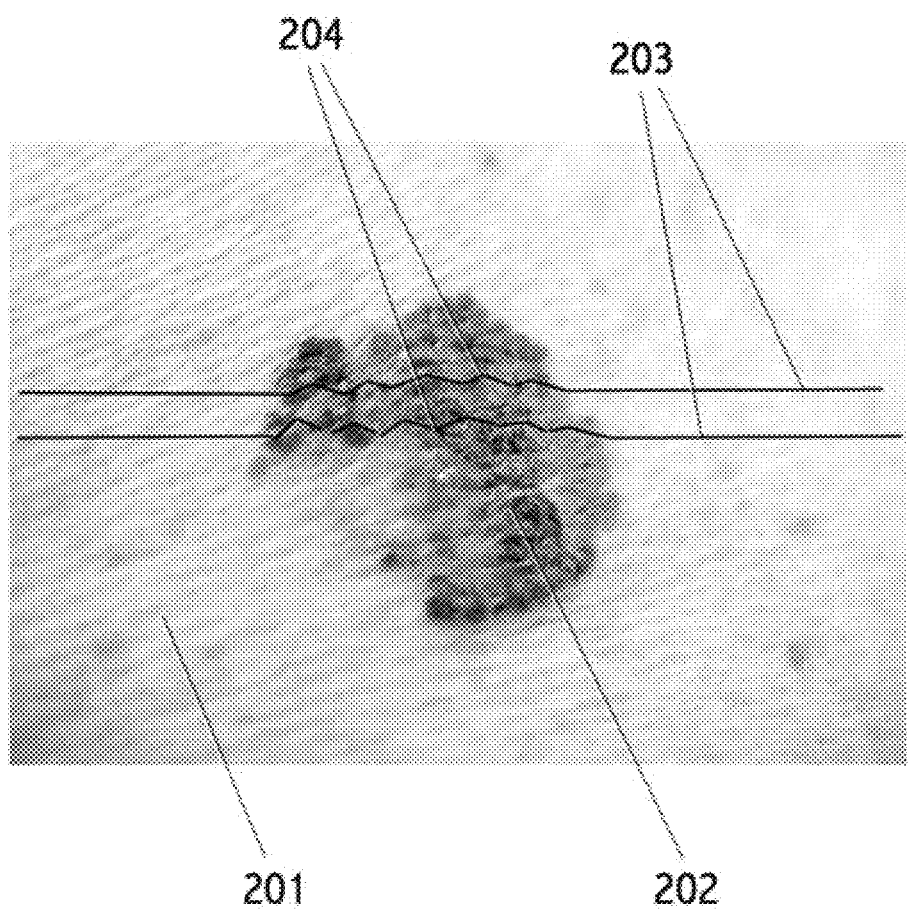
FIG. 12 shows an image of mole overlaid with two lines of pattern illumination.

In another embodiment of this invention, 3-D information about the area of interest may be captured and/or analyzed. On method of 3-D image capture uses a structured light source, such as a set of parallel lines, which may be generated by a laser or diode. FIG. 12 provides an example of an image useful for 3-D analysis. A second method of 3-D image-capture uses two lenses and two image sensors offset in a traditional "3D camera" arrangement.

Depending on embodiment, 3-D image capture provides three important medical benefits. First, the surface of the lesion may be analyzed to determine the quantitative elevation of the mole (if any) above the normal skin surface. This helps in the determination of lesion type. Second, the surface of the lesion may be analyzed to determine the amount and quality of mole texture or roughness. This helps in the determination of lesion type. Third, hair may be identified by either a human or by an automated algorithm far easier and more accurately in a 3-D image than in a 2-D image. Consistent and accurate identification of hair is necessary or beneficial for automated hair removal. Removing of hair from an image is important to improve the performance of other automated steps, such as determining the outline of a lesion.

Another problem with hair is that it can cause autofocus to focus on the hair, rather than the surface of the skin. Hair in an image may interfere with an automated algorithm to find the border of a lesion. Shaving a patient's skin can damage the skin or the lesion by causing micro lesions on the skin surface. Excluding patients with hair for use in studies may bias the study. Thus automated hair removal permits studies with less possible bias.

Fiducials

Figure 6A:
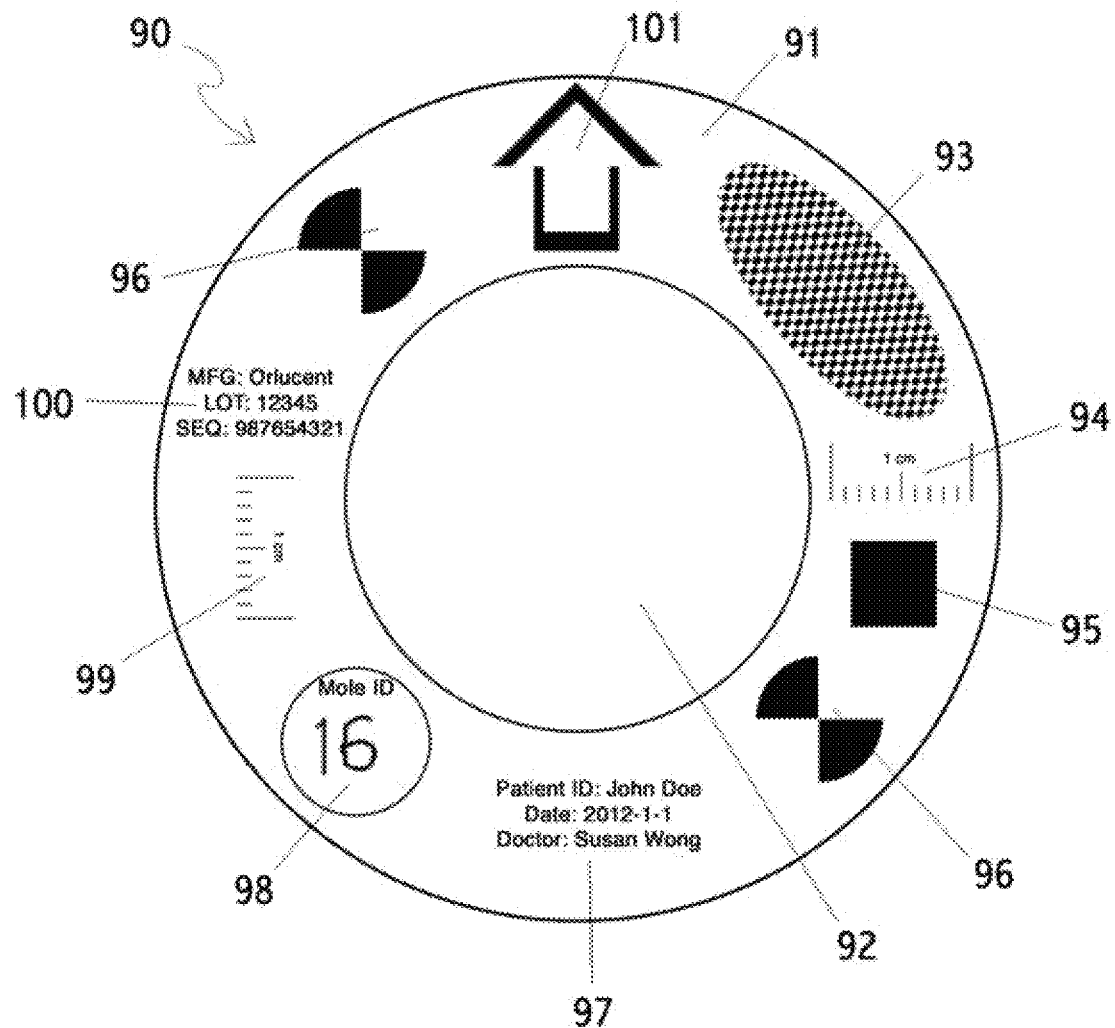
FIGS. 6a and 6b show one embodiment of a fiducial and a variation, respectively.

The fiducial, in one embodiment, is placed on the patient's skin next to the lesion of interest. FIG. 6a provides an example of a fiducial provided in accordance with an embodiment of the invention.

The fiducial, in another embodiment, can be tattooed on the patient's skin next to the lesion of interest.

A novel feature of one embodiment of this invention is the use of one or more multi-function fiducials. This embodiment provides time savings, cost savings, reduces medical errors, and/or permits significant post-photo automatic image processing and medical record keeping. Listed below are exemplary functions of fiducials, which are discussed in further detail below. Note that this invention includes all or a plurality of combinations of these functions in, methods and uses of one or more fiducials. In general, the more functions the better. Note, however, these individual functions or features are not isolated, independent benefits, but rather provide additional benefits when used as group, these benefits more than the sum of the individual benefits of the features. The use of singular fiducial or plural fiducials terminology is generally equivalent herein, unless specifically stated otherwise. Fiducial may refer to a single mark, a portion of a mark, or a set of marks, which may be on a single substrate for application or may be on multiple substrates.

Table 2, below lists fiducial features numbers, which are then discussed individual following the Table. Fiducial features appear alone or in combination in various embodiments.

TABLE 2

| Feature No. | Feature Description |
| --- | --- |
| 1 | Overall brightness of all visible fiducials comparable to brightness of the disease area of interest for image exposure control in the emission band |
| 2 | Brightness area of calibrated intensity for use in determining a metric of intensity in the disease area of interest |
| 3 | High contrast area for use as a focus or auto-focus target |
| 4 | Orientation of disease area of interest relative to the patient; anatomical terms of location on the patient |
| 5 | At least one pair of locations on the fiducial of a known linear distance separation for use in determining a size metric of one or more elements within the area of interest |
| 6 | At least one pair of locations on the fiducial for alignment of multiple images of the same area of interest taken at different light wavelengths |
| 7 | Identification of a specific area of interest on a patient where multiple areas of interest are imaged on a single patient. For example, this might be a numerical mole id number. |
| 8 | A tracking identifier to uniquely identify the specific medical diagnostic procedure being performed using this fiducial |
| 9 | Manufacturer and lot number of fiducial, with optional calibration information |
| 10 | Area in which machine printed information may be added at the time of the procedure |
| 11 | Area in which hand-written information may be added at the time of the procedure |
| 12 | Pre-printed fiducials |
| 13 | Fiducials with a combination of fluorescent marks with substantially the same excitation and emission spectra as the biotag and visible marks visible under visible light |
| 14 | Information to interface with an electronic medical records system. |

Fiducial feature 1 serves provides appropriate fluorescent brightness in the emission band to enable proper exposure, either preferably automatic exposure or manual exposure setting. Special area of the fiducial may be used to assure this, although generally the overall brightness of the entire area of interest is used for automatic exposure setting.

Fiducial feature 2 provides calibrated reference brightness so that the quantity or intensity of the biotag may be compared manually or automatically to a known reference for medical diagnostic purposes. Such calibration may be integral to the manufacturing of the fiducial or may be computed following the manufacture of the fiducial. The calibration data may be in reference to a specific lot number, and/or may be marked on the fiducial itself.

Fiducial feature 3 provides the ability to manually or preferable auto-focus the camera on the area of interest.

Fiducial feature 4 provides an important ability to locate the orientation of the area of interest with the anatomical orientation of the patient. As one example, an arrow on the fiducial may be aligned during the procedure to point towards the proximal or posterior location of the patient, as appropriate for the specific location and the preference of the medical practitioner. Or it may help the medical professional locate the mole in question where there may be multiple moles in close proximity to one and another.

Anatomical terms of location include, for example: anterior, posterior, dorsal, ventral, left, right, medial, proximal, distal, etc. Additionally, a body part may be identified such as an arm, the back, etc.

Fiducial feature 5 provides a known linear distance in or next to the area of interest to use in measuring any feature in the image, such as the diameter or circumference of a mole.

Fiducial feature 6 provides an important component of this invention, which is the ability to align multiple images taken with different wavelengths of light. Such alignment may be manual or preferably automatic. As discussed elsewhere herein, this feature allows a medical professional to accurately compare the image seen with visible light with the image created by the biotag. The marks to implement this fiducial feature must be visible in both visible light and in the emission band of the biotag. The marks do not have to appear identical in both wavelength images, but they do have to clearly align.

Note that because the cameras may be hand-held, or because the patient may move between exposures, images taken with visible and emission spectra light may not be naturally aligned. Thus, the fiducial feature 6 provides beneficial capabilities, as part of this invention, in one embodiment.

Fiducial feature 7 provides the ability to identify multiple areas on a patient. A patient might have 20 similar looking moles on his back, for example. It is important to know which mole is which when analyzing the resulting images.

Fiducial feature 8 permits an optional diagnostic procedure tracking code to be present on the fiducial. This could be a pre-printed number, unique to each manufactured fiducial. Or, it could be an identifier added at the time of the procedure. It might be human readable, machine readable, or both. A machine-readable diagnostic procedure identification aids substantially in permitting automated medical record keeping and in reducing medical errors. The tracking code may or may not be visibly discernable. A signal may be emitted from a fiducial.

Fiducial feature 9 permits accurate tracking of fiducial manufacturing and quality. Like drugs, it is often valuable to identify a manufacturer and lot number for quality control, inventory, expiration date, and other purposes.

Fiducial feature 10 permits a manufactured fiducial with most of these features to be customized at the time of the diagnostic procedure. Such customization would typically include the patient's name or patient ID number or other ID number, and may include the date, physician's name or other information unique to the procedure. This information may be hand entered or preferably machine printed. Note that this information does not need to be visible in the emission spectra, because the visible light and emission spectra light images will be lined or merged, however, such visibility in the emission spectra is preferred. One method of such printing is to use an ink-jet printer with fluorescent ink.

Fiducial feature 11 permits a medical practitioner to add information to the fiducial by hand at the time of the diagnostic procedure. This feature allows the practitioner to add information desired by the practitioner or relevant to the particular area of interest. For example, the practitioner may enter a mole number as the fiducial is applied to each mole.

Fiducial features 10 and 11 are particularly valuable based on the way many medical diagnostic procedures are performed. For example, in one part of an office, clinic or hospital, the fiducial may be prepared using feature 10 a few minutes or hours in advance, based on a scheduled appointment, along with other lab preparation. Then feature 11 is used by the physician or technician immediately before or after the fiducial is applied to the patient. Thus feature 10 is most applicable to the scheduling of appointments and feature 11 is most applicable during the procedure itself.

Fiducial feature 12 allows fiducial to be manufactured in advance. Each fiducial may be provided with both standardized and unique information, such as a sequence number or lot number.

Fiducial feature 13 allows fiducials to have a combination of marks, some of which are visible in the emission band of the biotag and some of which are visible in the visible light band. Because images of an area of interest taken in visible light and in the emission light band are merged, overlaid or linked, both types of marks will be visible and useable in analyzing the diagnostic procedure results.

Note that some of these features may be combined into a single mark or group of marks. That is, a single mark on a fiducial may serve more than one purpose.

The reference to "at least a pair" of marks may refer to two or more portions of a single mark. For example, a single rectangle could serve as linear measure by using two sides of the rectangle. As another example, a single circle could be used to align images by using more than one portion of the circle for alignment.

In some embodiments, a fiducial may be on a single substrate, such as tape or carrier, which may or may not stay with the fiducial when placed on the patient. Or multiple individual physical fiducial components may be placed on the patient. One embodiment uses a donut shaped fiducial carrier that surrounds the disease area of interest.

In one embodiment, fluorescent dye or compounds are placed within a polymer in the fiducial so that the dye or compound will not exit the polymer or enter the patient's skin. The polymer may prevent degradation of the fiducial and may assist in the stabilization of the fluorescent compounds. The polymer may prevent diffusion and assist in prevention of a change of the calibration of the fiducial. The polymer may block stray or unnecessary light from entering the fiducial. The polymer may be a coating on the fiducial, or it may be integral with the fluorescent compounds.

The fiducial may use more than one fluorescent dye or compound. In some embodiments, the dye or compound is not identical to a fluorescent marker in the biotag.

Complex fiducials may be cut or modified during the diagnostic procedure to accommodate special locations. For example, a mole in the crease of skin next to the nose may not accommodate a donut-shaped fiducial. Various shapes of fiducials may be created or selected for various locations on a subject's body.

A fiducial may be permanently implanted on the patient for long-term tracking.

Note that the shapes and arrangement of marks on the fiducials may vary considerably from the examples herein.

Optical System

A novel feature of this invention is the use of an integrated optical system. The integrated optical system may be a consumer or prosumer digital SLR camera, for example. By integrated, it is meant that the camera body may include a power-supply such as a battery, an internal image sensor, internal image storage memory, user controls conveniently on the body, at least one user display, internal autofocus logic, internal control electronics including stored instructions for an embedded processor, and/or internal image processing logic including stored instructions for an embedded processor. We refer to the integrated optical system as a camera in this disclosure. Any discussion herein of a camera may apply to any integrated optical system and vice versa. The camera body is either attached to or includes a non-interchangeable lens, preferably a macro-lens, or the camera body accepts interchangeable lenses. For this invention, a macro-focusing lens is preferable.

Prior art cameras are not integrated. That is, generally, the necessary components and controls for operation are not contained in the body of the camera, and the camera is not manufactured in high volume. As such, they are rarely suitable for hand-held operation. They are also expensive, as they are designed and built specially for a medical application.

Modifying an "off-the-shelf," or "consumer" camera for this special purpose medical application has several obvious benefits: the camera is low cost, reliable, self-contained, easily hand-held, and/or includes key components such as a complete user interface, image display, auto-focus, and/or image storage. A key reason why such an approach has not been used before is that fluorescent biomarkers operate in the infrared (IR) spectrum. Consumer cameras do not operate in the infrared for at least one reason: the image sensor is covered with an IR filter to block IR light. The camera would not operate properly in the visible spectrum without an IR filter. A second reason consumer cameras with phase-detection auto focus will not work in this application is that the autofocus sensor and algorithms work only with visible light, not with IR light.

It might be possible to configure a fixed-focus camera to work in the IR spectrum. However, a fixed focus camera with a reasonably high numerical aperture will have different focus points for visible and IR light. To be practical, in one embodiment, in this medical application, the camera preferably takes two pictures of the target lesion: one in the visible spectra one in the IR spectra looking at the emission from the biomarker. The visible light spectral image is useful in order to correlate the glowing areas in the IR image with the exact area of skin on the patient. That is, the lesion needs to be accurately located. It is also valuable to the physician to accurately compare what the physician sees, that is, the visible light image, with what has been detected as cancerous with the biomarker. This comparison is critical to answer such questions as: (a) Are the visible lesion and cancerous lesion the same size and shape? (b) Is the cancerous portion of this lesion directly underneath the visible lesion? (c) Is only a part of the visible lesion cancerous? (d) Has the cancerous lesion spread beyond the visible lesion? (e) Are the cancerous lesion and the visible lesion separate growths? (f) Is the signal from the lesion in question or one on the periphery? Answers to such questions may aid in diagnosis.

A preferable size for detection can be below 25 mm in diameter and is not limited to lesions above 5-6 mm in diameter. Lesions below 1, 2, 3, 4, 5, or 6 mm in diameter can be imaged and/or analyzed.

Auto-focus becomes more critical or useful when: (a) the numerical aperture is larger, (b) the lens is closer to the subject, (c) the magnification is higher, or (d) the resolution is higher. The combination of these four factors, when implemented suitably for this application, is such that auto-focus becomes a practical necessity if the camera is to image both visible and IR light. A medical camera using visible light for one image and IR for a second image, using a lens with a high numerical aperture, requires the use of autofocus because the focus at the two different wavelengths will be different. The use of the camera's built-in autofocus mechanism for these dual purposes is both novel and a major benefit of this invention.

There are two major types of autofocus used today, along with minor variations. We describe each separately, and each of these two types of autofocus is a separate embodiment of this invention. Various types of autofocus can be incorporated alone or in combination with the invention.

The first type of autofocus (AF) we describe we call contrast detection, although various terms exist in the art. Contrast detection is characterized by searching for the focal point that generates either the highest spatial frequency components in the image, the most high-spatial frequency components in the image, or the most contrast in the image, or some combination or equivalent. The focus may be mechanically adjusted by moving the lens, moving an element within the optical path, moving the image sensor, or by other means. This approach is most commonly used in cameras with no mirror and/or using the image sensor for the autofocus, however, other implementations are possible. For example, a mirror may be partially transparent.

Contrast detection autofocus is suitable for one embodiment of this invention with no changes to the autofocus algorithm or firmware, or mechanical focus mechanisms. However, some improvement may be possible by changing either.

The second type of autofocus (AF) we describe we call phase detection, although various terms exist in the art. Phase detection is characterized by the use of an additional sensor besides the image sensor, which has at least the function of autofocus: the AF sensor. A beam splitter, and/or a partially reflective mirror, or other means is used to direct light from the subject to the AF sensor. Two micro-lenses capture the light rays coming from the opposite sides of the lens and divert it to the AF sensor, creating a simple rangefinder with a base within the lens's diameter. The two images are then analyzed for similar light intensity patterns (peaks and valleys) and the separation error is calculated in order to find if the object is in front focus or back focus position. This quickly gives the direction of focusing and amount of focus correction needed. This more complete information typically allows faster focusing than contrast detection.

However, when using phase detection AF in the IR, it is necessary to change the firmware in the camera because the separation error is different for IR than for visible light. Thus, in embodiments of this invention that use phase detection AF, the autofocus firmware is modified to look for peak detection where the peak separation is in the emission band being used, rather than the peak separate for visible light. In the simplest case, this involves updating single constant in the firmware.

For this invention, in the embodiment using phase detection AF, the camera's internal IR blocking filter that is in the optical path of the AF sensor is removed.

Autofocus, when using light in the emission spectra of the biotag, may either be on the biotag itself, if present, or on the fiducials. The use of the fiducials assures proper autofocus, even if the biotag is missing, weak or diffuse.

Spectra Considerations

Detection of the biomarker comprises exciting the detectable label portion of the biomarker with light of an excitation wavelength, then imaging the resultant longer emission wavelength light emitted by the label. Ideally, there is no overlap in the useful excitation spectra and the useful emission spectra of the entire optical system. Any overlap would cause some of the excitation light to be in the image, whereas ideally no emission light would in the image. In some implementations, some overlap may occur.

As in all imaging, an important goal is to have a high signal to noise ratio. That is, have the most light from the target of interest, in this case cells with the biotag attached, and the least light from all other sources. In general, the brighter the excitation light, the brighter the emission light. Thus, one wishes to concentrate as much of the excitation light in the most sensitive area of the excitation spectrum. A primary source of undesirable light is the excitation light being picked up in the emission photograph. Thus, one wants as little of the excitation light as possible to be seen in the emission photograph. Both of these goals are accomplished by specific elements of one embodiment of this invention, as described in detail below.

Another source of undesirable artifacts in the medical image is inconsistent illumination. Such lighting inconsistencies take many forms, including vignetting or blotchy illumination. These inconsistencies make calibrated readings difficult or impossible. However, at the same time, one wishes to concentrate the energy used for excitation light into the area of interest. Uniform illumination is typically at odds with such efficient illumination. Certain aspects of some embodiments of this invention optimize both of these goals, in particular the design of the LED lighting sources and diffuser, as will be explained in detail, below.

The "useful" excitation and emission spectra, including the final signal to noise ratio, depends on the end-to-end performance of the complete optical system. The major elements to consider for the spectral analysis of the system include one or more of the following: illumination LED driver electronics; illumination LED(s); illumination filter; excitation spectra of the fluorescent compound(s); emission spectra of the fluorescent compound(s); emission filter; lens; IR filter (if any) covering the image sensor; image sensor; image processing. The shape of emission spectra, filter spectrum, emission spectra, or sensitivity spectra for all components is called, simply, "spectra" herein. The spectra for LED(s), and excitation and emission of the biomarker are frequently peak shaped. The spectra for the filters are frequently box-shaped with steep sides. The spectra for the skin, lens(s) and image sensor are more or less one-sided, with uneven, non-steep slopes on the declining side.

This invention includes but is not limited to novelty in the selection, positioning and implementation of specific components in the optical chain, in order to achieve improved performance, cost reduction, and convenience.

Major factors for each element in the optical chain that contribute to final image quality include spectra, mechanical alignment in all axis, and optical uniformity. The physical elements in the imaging chain comprise the following, in nominal optical sequence:

Electronic drive for the illumination LED(s)
Illumination LED(s)
Illumination lens(s) and diffusers
Illumination filter
Subject skin Subject lesion
Biomarker mechanical, spectral and optical performance
Emission filter
Imaging lens
IR filter (if any) over image sensor
Image sensor
Image processing electronics and algorithms Any of these physical elements may be provided optionally. Additional physical elements may be provided. In some instances, the sequence of one or more of the physical elements may be altered.

There are numerous other elements that have an impact on the final image quality. Some of these include:

Scattered light in the optical system
Dust and other contaminants in the optical system
Alignment of optical components
Imperfect optical component, such as vignetting, distortion, noise, absorption, internal reflections, and degradation over time
Non-uniform illumination
Defects or variations in the image sensor
Mathematical weaknesses in the image processing algorithms
Inconsistencies of components due to manufacturing variations
Misalignment of the device by the operator
Motion of the device in use
Motion of the subject during exposure
Autofocus errors
Irregularities in the subject distance over the field of view
Image Viewing A preferable embodiment uses a macro lens.

A preferable embodiment for viewing the visible light image and the emission light image is on a dynamic, electronic display, where the user interface may include a slider or equivalent means to continuously change the image seen from the visible light image to the emission light image, and back, where the two images have been automatically aligned.

A preferable embodiment for delivery of automated melanoma detection is to match the features of the mole under review with features extracted from an image library using supervised learning. The mole under consideration has its features measured automatically during image processing. Currently, 28 features are considered out of over 300 identified, including texture, size, etc. Any number of features may be considered during image processing, and the library may have any size. These extracted features are compared with the features previously extracted from the image library and classification is based on best match. Classification is to provide images from an image library ("reference images") that match as closely as possible the patient's mole or area of interest. The library images have previously been characterized, for example, by mole type and cancerous content, if any. In addition, a preferable embodiment provides one or more quantitative assessments of how closely the patient images match the reference images. Ideally, but not necessary, these quantitative assessments represent a percent likelihood that the patient's area of interest is the same mole type or cancer type (or disease) as the patient's area of interest.

In one embodiment a dynamic slider is used to compare two overlaid images where one image is from the patient and the other image is a reference image, presented either at the same effective resolution or such that the diameter of the mole or cancer is matched between the two images.

FIG. 1 provides a block diagram of a device used in accordance with an embodiment of the invention 14. Shown is the integrated imaging device 1. The integrated imaging device may have a cavity for a memory card 2, which may include a wireless interface (not shown in the Figure), a user display 3, and a user control 29. The user display can include a screen or other display that may show an image that may be captured by the integrated imaging device. A lens may be provided or attached to the integrated imaging device. The lens 13 is either integral to the integrated imaging device or the device is adapted to accept interchangeable lenses and one such lens, ideally a macro lens, is shown installed on the camera as 13. An operating button 4 may also be integrated within the integrated imaging device. Other user interface mechanisms such as touchscreens, levers, sliders, knobs or features may be used for a user to interface with or interact with the integrated imaging device.

One or more filters may be provided in the integrated imaging device, attachable to the integrated imaging device, or can interact with the integrated imaging device. The integrated device may have two filters, 5 and 6 in a means, here shown as a slide 12, to move the filters respectively into the optical path of the camera. Any number of filters (e.g., 1, 2, 3, 4, 5 or more) may be provided. The filters may pass different wavelengths of electromagnetic radiation to pass through, relative to one another. The filters may be movable relative to the optical path of the camera and/or one another. The filters may move orthogonal to the optical path of the camera. Desired filters can be slid, pivoted, or rotated into place. Filter 5 is a visible band pass filter and filter 6 is a fluorescent emission band pass filter. A white light source 7, can be provided. The white light source may comprise white LEDs or any other light source. A fluorescent excitation light source 8, could comprise infrared LEDs. Two fluorescent excitation light sources are shown in order to achieve uniform illumination of the mole or other target area. Uniform illumination is advantageous in achieving a calibrated or measurable response based on the biotag and/or the fiducials for this purpose. Fluorescent excitation band pass filters 9, may be provided between the fluorescent excitation light sources 8 and the subject 11. The excitation band pass filters may be provided between the excitation light sources and an area of interest or cavity and/or tissue surface of the subject. A structured light illumination component 10, such as a diffuser may be provided, which may be integrated with one or both white light sources 7 in order to achieve uniform white light illumination of the subject. The diffuser may be an optical element that may diffuse or spread light.

Continuing with FIG. 1a, a light source 15 may be provided comprising the emission wavelength of the biotag. A narrow-pass-band filter 16 can be used to restrict the light from 15 to just the emission wavelength, at least for the wavelengths sensitive to the camera. The combination of the light source 15 and filter 16 may be used in an autofocus embodiment, discussed elsewhere herein. The filter 16 may not be required in all embodiments when the light source 15 is sufficiently narrow-band. The light source 15 may be an LED, laser, fluorescent emitter, or other light source. Similarly, filter 9 may not be required in all embodiments when the light source 8 is sufficiently narrow band. 8 may be LED, laser, fluorescent emitter, or other light source.

Note that the elements shown in FIG. 1a are not to scale and the arrangement of the elements as shown is purely exemplary. The number of illumination elements may be two, as shown, or may be one element, or more than two elements. Light directing elements such as mirrors, prisms, light-pipes, fiber optics or splitters may be used to direct the light. Not all elements are required in all embodiments. In particular, the moving filters 5 and 6 in slide 12 may be required in some embodiments, as discussed in more detail elsewhere herein.

In one embodiment a single filter is used, instead of two. In this single-filter configuration, the filter has a band-reject notch at the excitation frequency, such as 660 nm, while letting both visible and emission band light pass. In this way, such a single filter may be used, without changing filters, for both visible and emission exposures.

Structured illumination may be used to identify hair. The structured illumination may also be used to determine the height and shape of the mole above the surface of the skin, and the texture of the mole. One type of structured illumination is used to shine a series of a parallel light beams at a low angle to the skin. When photographed from an angle approximately normal to the skin, the light beams will appear as parallel, straight on a flat surface, but will be distorted, non-straight, based on elevation and texture. Hair will be visible as major discontinuities in the parallel light beams. One method of achieving structured illumination is with a diffuser with a series of parallel slits in front of a white light source, through which are projected parallel beams of light. A second method is to use an image plate, which provides a series of brightly lit white lines, then use a lens to image this image plate onto the skin. The image plate may be a piece of clear plastic with grooves machined in it, or an illuminated plate overlaid with an opaque filter with transparent slits for the lines. A third method of achieving structured illumination is with a series of parallel cylindrical lenses in front of a white light source. Structured illumination could be included, in some embodiments, as the shape of the plastic encapsulation over one or more LEDs. Yet another embodiment uses an interference pattern from laser light to create the parallel lines of light. One embodiment of structured illumination is show in FIG. 12.

Figure 1B:
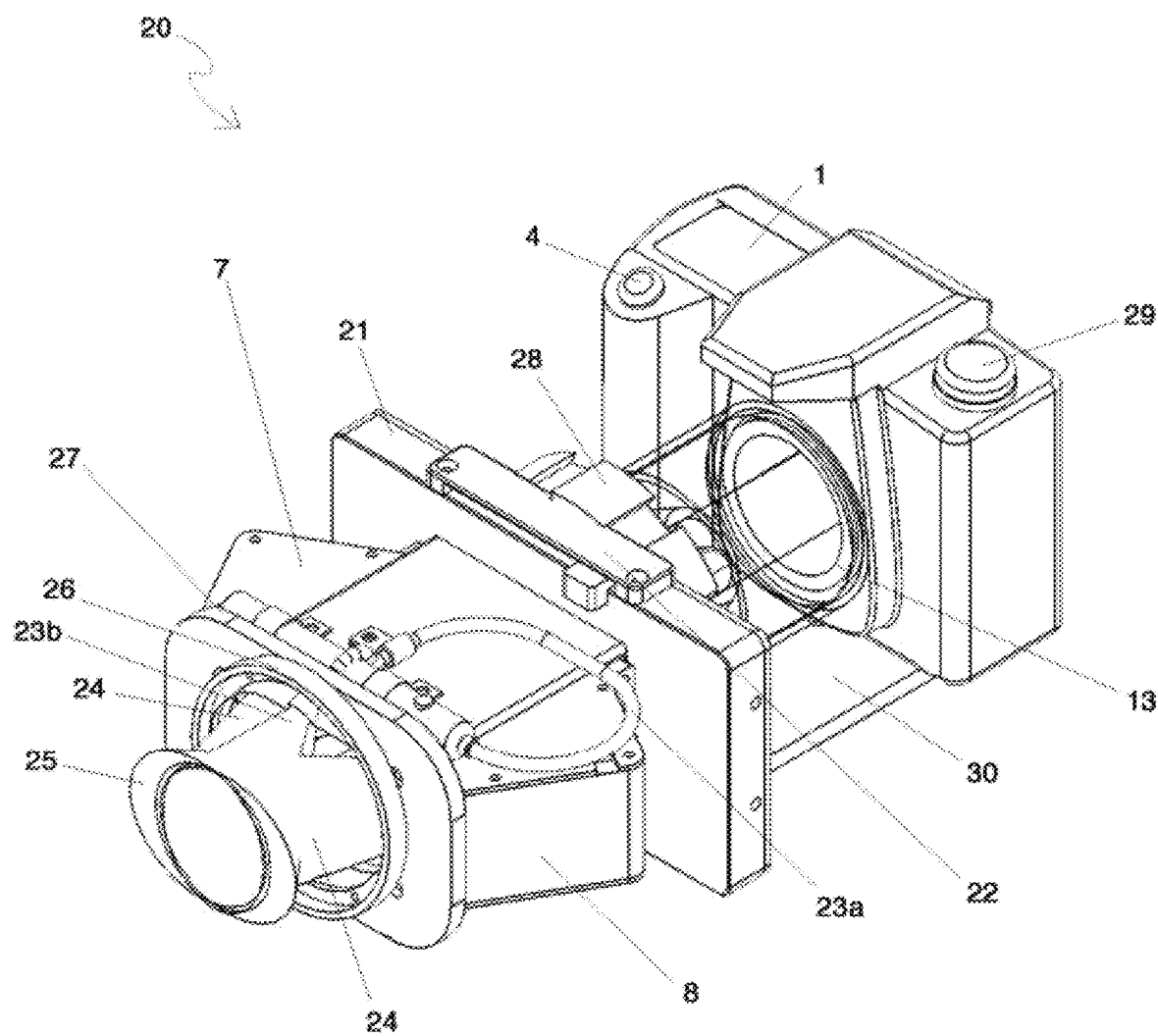
FIG. 1b shows a wire-frame isometric view of the camera, in one embodiment.

FIG. 1*b* provides a wire-frame view 20 of a system in accordance with an embodiment of the invention. Shown is the integrated imaging device 1, with an operating button 4. The user display 3 and memory card cavity 2 are not visible in this view. Filters 5 and 6 are not visible in this view. The filters 5 and 6 may be inside of the filter holder 21. Filters 5 and 6 may be moved in or out of the optical path by activating a slide 22. The white module 8 holds white LEDs, drive batteries, and/or the structured light illumination component 10, not visible in this view. The fluorescent emission light module 7 also holds drive batteries and/or the fluorescent band pass filter 9, not directly visible in this view. A mounting ring 13 may be provided for an interchangeable lens. The mechanical components are held in position rigidly by a mounting plate 30. An attachment point 27 may be provided for a light baffle. This drawing shows two converging light sources, from 7 and 8, as two light beams 24. These two light sources can illuminate the target area 25 uniformly. Optionally, a diffuser or other optical elements may be provided to assist with uniformity of illumination.

In some embodiments, a white LED 23*a* may be provided at one end of a plastic fiber. The other end of the plastic fiber provides the white light 23*b* to illuminate the area of interest 25. The fiber may be an optical fiber capable of conveying light from a first end to a second end.

Compartments 7 and 8 hold illumination LEDs, and optionally batteries or other power sources for the LEDs. Alternatively, power for the illumination light may be provided the battery in the integrated imaging device 1, or by a connector (not shown in FIG. 1*b*) to an external power source. Power may be provided in various combinations. Compartments 7 and 8 may also hold other illumination sources such as elements 15 and 16 shown in FIG. 1*a*. Compartments 7, 8 and/or 15 may be combined, or missing entirely from some embodiments.

A ring 26 may be used for providing white light ring illumination. A structural component 27 of the invention may be used as a camera-end termination for a light baffle (not shown in FIG. 1*b*).

No structured light illumination is shown in FIG. 1*b*.

An alternative white light ring illuminator may be provided in accordance with some embodiments of the invention.

FIG. 2*a* shows a block diagram of the steps in a method for use of one embodiment for medical diagnosis. Note that all terms used are defined in this description. All steps are further defined and discussed with alternative embodiments elsewhere in this description. The medical professional first places the biotag topically on the mole or other area of interest 31. In alternate embodiments, the biotag can be injected or applied to an area of interest in other manners. Any description of a mole may apply to a lesion or other area of interest, or vice versa. After a short incubation period the medical professional removes the excess biotag 32. The incubation period may be any predetermined period of time. The medical professional places one or more fiducials close the mole 33. The fiducial may be within an area of interest or adjacent to an area of interest. The fiducial may be proximal to an area of interest, for example within 30 mm, 25 mm, 20 mm, 15 mm, 12 mm, 10 mm, 8 mm, 7 mm, 6 mm, 5 mm, 4 mm, 3 mm, 2 mm, or 1 mm of a mole, lesion or area of interest. This step may be prior to steps 31 or 32, however the order shown in this Figure is preferred. A user may then set the visible mode of the camera, and place the camera in position (or the patient in position) to block stray light, typically with the use of baffle and take an image using visible light 34. The user may be a medical professional. The medical professional then sets the camera to fluorescent mode and captures an image using the fluorescence of the biotag, 35. 34 and 35 may be performed in the reverse order. Finally, all taken images from this patient are transferred out of the camera, preferably via wireless, 36. However, a memory module or wire may alternatively be used to transfer images. Data from a camera may be transferred to one or more external devices. The data may be transferred wirelessly or via a wired connection. Data may be transferred directly to the one or more external devices or over a network.

Often, a patient can have more than one mole. The entire process can be repeated for each area of interest on the patient. For convenience, step 31 may be performed first for all moles, followed by 32 for all moles, then step 33 for all moles. Note that one capability of this invention is the use of a combined fiducial to identify which mole is which on the patient. Thus as step 33 is repeated the medical professional ideally either selects or writes on the fiducial prior to placement to identify the mole. Preferably, all image for one patient step 36, is transferred at the same time. Clearly, for multiple areas of interest, steps may be performed in various orders.

FIG. 2*b* shows a block diagram of steps in a method for computerized image analysis of the images taken in this invention. Step 41 starts with importing the images from the camera, ideally but not necessarily wirelessly. A computer, general purpose or specific purpose is used for some or all of the steps in this Figure. A processor can be used for some or all of the steps. Such a processor can be within the camera. Alternatively, it may on a PC, laptop, server, tablet, mobile device or in the internet cloud. Computerized image processing may be performed in the camera, using its embedded processor, or on a computer, tablet, smart phone or other electronic computational device. The steps of image processing are commonly split among multiple devices.

Instructions and data reside in computer readable media and/or memory. Step 42 uses the visible light image to locate the mole borders. Then, in step 43 the color and texture are extracted from the visible light image in within the determined mole borders. In steps 44 and 45 the locator fiducials, as discussed elsewhere in this specification are located on both the visible and fluorescent image; these two steps may be performed in either order, and may be performed prior to 41, 42, or 43. Then, in step 46 the two images, the visible light and the fluorescent light, are aligned using the locator fiducials from the prior two steps. In step 47, mole features are extracted from one or both images. This extraction is responsive to the known mole borders. For visible light images, which have been used traditionally to classify moles, classification 48 is predominantly within the mole border. Supervised machine learning is performed on the library of images. Classification of moles is based on the features, or "characteristics," learned from the library. Features calculated from the image under review are compared to the distribution of features in the library.

Characteristics such as size, uniformity, texture and color are often considered. The biotag provides significantly improved diagnostic information, as the biotag is visible in the fluorescent image for diseased cells only. The cancerous cells may extend beyond the border of the visible mole. Classification 48 against library images using the fluorescent image, or in combination with both images is likely to produce more accurate diagnosis. Finally, the images are presented to the medical professional 49. Ideally the visible light image and the fluorescent light image are presented as an overly, where the medical professional, using a slider or similar means, can dynamically change the overlay from 100% one image to 100% the other image as a way to easily see how the two images align. Also, matching images from the library are presented, along with quantitative matching coefficients and information about the library images. One or more of the steps described herein may be optional, additional steps may be provided, or order of the steps may be altered.

FIG. 3a shows a cutaway view of the camera of this invention. The integrated imaging device body 1 contains a user-viewing screen 51. Plate 30 holds the camera components rigid. A primary optical path 61 of the camera may go through a lens 13. A primary optical path may terminate at an area of interest. The two filters 5 and 6 previously described are shown visible in the filter holder 21. Filter 5 is in the optical path in this drawing. The white light 7 and fluorescent excitation light 8 modules can be included as previously described. The locations of the white LEDs 54 and the fluorescent excitation LEDs 60 in their respective modules are shown. Fluorescent excitation band pass filter 9, previously described is shown. The structured illumination component 10, previously described, is shown. The paths of the white light 57 and 58 and fluorescent excitation light 59 and 24 can be provided. The area of interest 25 may be provided. A compartment 56 for illumination batteries and power drive electronics for the illuminators may be included.

FIG. 3b shows a perspective view of the camera. The integrated imaging device body 1 contains a user-viewing screen 51. Plate 30 holds the camera components rigid. 13 is the lens. 21 holds the two filters 5 and 6, not visible in this view. Filters are selected by the slide 22. 7 and 8 are the white light module and the fluorescent excitation light modules, as previously described. 62 is the flexible light baffle. The flexible light baffle may prevent undesirable light from entering the field of view. The flexible light baffle may prevent ambient light from reaching an area of interest, or reduce the amount of ambient light. The flexible light baffle may be flexible to accommodate surfaces of varying shapes or topologies.

One or more components described herein may be removable. For instance, one or more attachment having one or more filter and/or light source may be added to a camera. The attachment may be permanently or removably attached to the camera. In some instances, multiple levels or stages may be provided that may be added to the camera.

FIG. 4 shows a visible light photograph of a mole. In this figure the photograph is shown in black and white. The original photograph is in color. Visible light photographs may be in black and white, color, monochromatic, or any other color scheme. 71 is a mole. 72 and 73 are two fiducials. These two fiducials can serve as both color references and as locator fiducials. Fiducials may have other features or uses as described elsewhere herein. The fiducials may or may not be located at a known distance from the moles. The fiducials may or may not have a known size.

Figure 5:
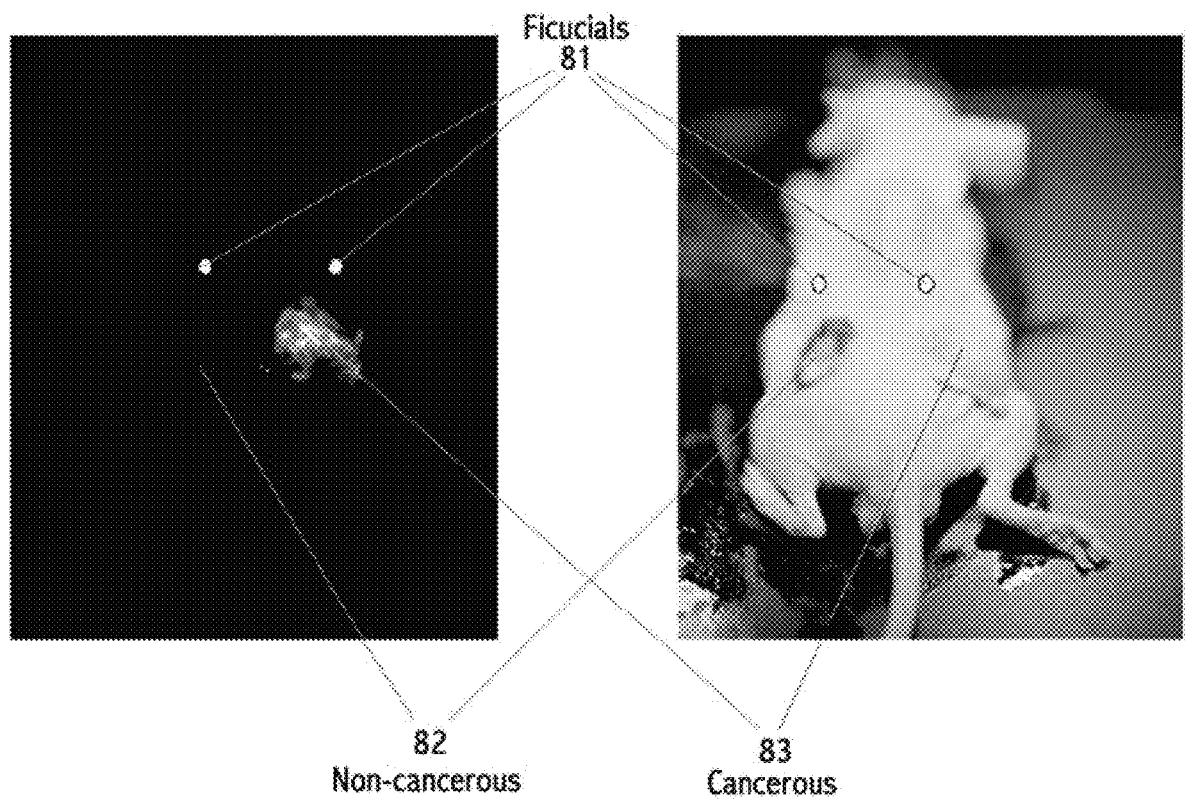
FIG. 5 shows two black and white photographs of a skin tumor and benign skin growth and fiducials in IR light and in white light.

FIG. 5 shows both a visible light photograph on the right and fluorescent photograph on the left of the same subject: a mouse with both a cancerous and a non-cancerous lesion. 81 show the two fiducials in both photographs serve both as locator fiducials to align the two images when overlaid and as biotag emission reference brightness fiducials, as can be seen on the left image. 82 point so the non-cancerous lesion in both photos. 83 points to the cancerous lesion in both images. As can be seen the non-cancerous image is nearly invisible in the fluorescent photo on the left.

Such images may be captured using the same device. For instance the same device can be used to capture a visible light photograph and a fluorescent photograph. The same device can be used to capture a plurality of images, wherein at least some of the plurality of images were captured under different wavelengths of light. The images may be viewed separately and/or overlaid on one another. One or more of the images may show a biotag in a visibly discernible manner. One or more of the images may not show the biotag in a visibly discernible manner.

FIG. 6a shows a fiducial 90 in accordance with some embodiments of this invention. Not all embodiments and not all features are necessarily used in any one embodiment, application, device, method or use. The term fiducial can either refer to a physical object, such as printing, ink and die on a substrate, typically a plastic film suitable for placing on skin, or to a particular mark on that substrate. The fiducial may optionally have an adhesive or other feature that may permit it to attach to a surface, such as a subject's skin. Thus the singular fiducial and the plural fiducials are typically used interchangeably, subject to context. Here the substrate 91 is in the shape of donut, allowing a mole, lesion or other area of interest to be in the center hole 92 of the physical substrate. The fiducial may be sized and/or shaped at least partially surround the area of interest. Many other shapes are possible, including individual dots, circles, ellipses, rectangles, or crescents. Fiducials are discussed in more detail elsewhere in this disclosure. A direction fiducial 101 provides anatomical orientation on the patient. An exposure and focus fiducial 93, in this example as single area providing two functions, in conjunction with the other fiducials used on the patient for the same exposure, provides sufficient area for auto-exposure setting by the camera, and in this example provides a grid with many high-frequency edges in at least axis for quality auto-focus by the camera. 94 and 99 provide two scales for accurate measurement(s) of the mole or lesion. Note that in this example they are orthogonal. In some embodiments, it is advantageous if the camera or subject may be significantly non-normal to the area of interest. 95 provides a solid area for quantitative calibration of the brightness of the biotag in the fluorescent image. 96 consists of two locator fiducials that are used either manually or preferable automatically to align the visible light and fluorescent light images. 97 is an area or text to identify the patient and/or medical professional and/or procedure. Depending on embodiment, this area is pre-printed during the manufacture of the fiducial; machine printed at the office prior to imaging, or hand printed. 98 provides and area in which the medical professional may handwrite. It is also an area to identify the particular mole on a patient with more than one area of interest. 100 provides medical tracking information such as manufacturer ID, a LOT number and/or a sequence number. The sequence number may be used, in conjunction with medical records, to identify the procedure. Thus, this could be used an alternative to 97. In some cases fiducial marks can be combined to provide more than one function.

Figure 6B:

One or more of the features described herein may be provided within a fiducial. A fiducial may be a multi-function fiducial which may combine a plurality of the features discussed herein. A fiducial may be formed from a material that is not visible in a predetermined emission spectra. The fiducial may have one or more marks on the base that is formed from such a material. The aggregate of all marks created at the original time of manufacture of the fiducial may have a predetermined exposure brightness in the predetermined emission spectra when exposed to light in the predetermined excitation spectra. In FIG. 6*b* a machine-readable code is shown 102. In this case the code is a QR code that contains the same information as ID area 97 in FIG. 6*a*. Such a machine-readable code could be used on a fiducial for automated medical records and as a way to reduce errors in reduce costs, as a benefit. Any form of identifier may be used. The identifier may be optically readable. The identifier may emit a signal that may be read by another device. The signal may be a visible signal, RF signal, IR signal, wireless signal, or any other type of signal.

Figure 7:
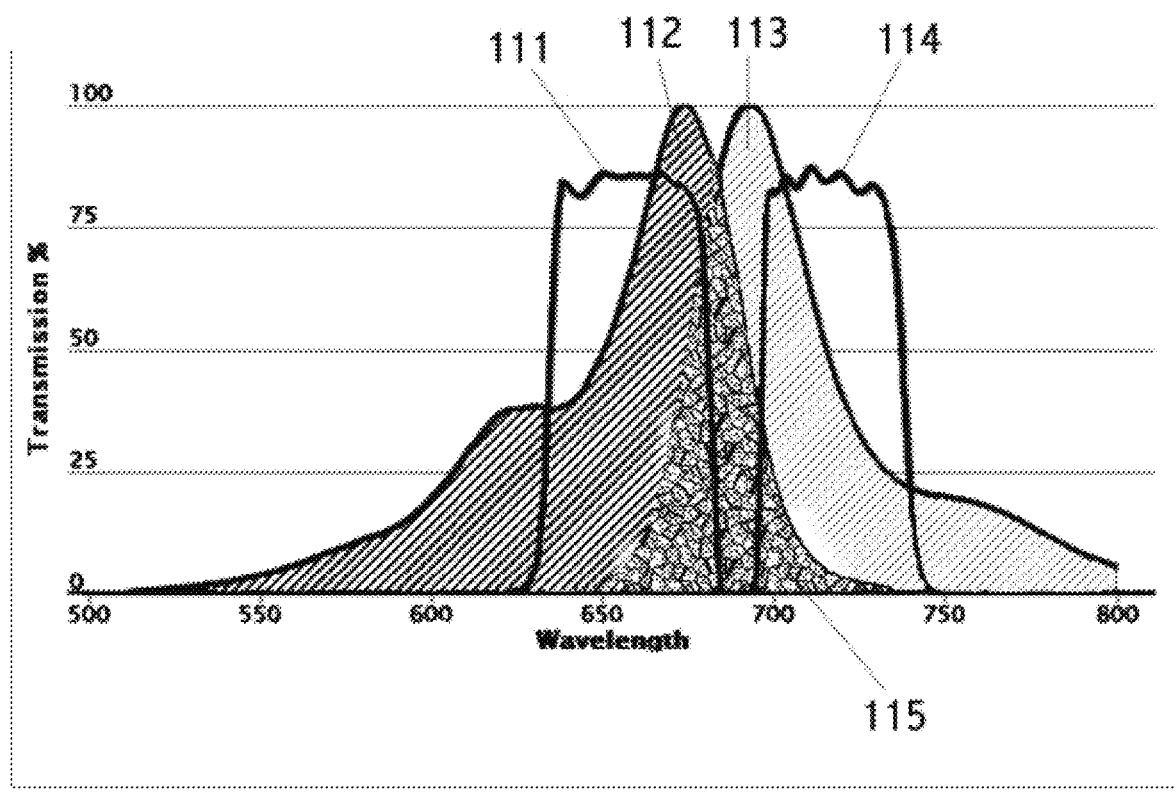
FIG. 7 shows one embodiment of fluorescent marker selection and associated light spectra and filter spectra.

FIG. 7 shows the relationship between various special bands used in one embodiment of this invention. The horizontal axis shows wavelength in nanometers and the vertical axis is percent from 0 to 100%. Curve 112 is the excitation band for Cy 5.5 Fluorophore, showing excitation efficiency vs. wavelength. Curve 113 is the emission band for Cy 5.5 Fluorophore, showing emission amplitude vs. wavelength. Both curves are normalized with 100 at the peak. Curve 111 is the fluorescence excitation band pass filter spectral transmission v. wavelength, as used in one embodiment. Curve 114 is the fluorescence emission band pass filter spectral transmission v. wavelength, as used in one embodiment. 115 is the area of overlap of the curves 112 and 113.

Not shown in this Figure but relevant to the design and implementation are the spectral curves for the LEDs, lens optics, sensor, and image processing.

FIGS. 8*a* and 8*b* show a benign mole topically treated with a biotag in visible light and IR light, respectively. FIGS. 9*a* and 9*b* show a recurring melanoma mole topically treated with a biotag in visible light and IR light, respectively.

121 is the visible benign mole. 122 is the visible recurring melanoma mole. FIG. 8*b* is almost completely dark, indicating no melanoma cells. A faint border 124 is visible around the mole 123, which is the region of the skin on which the biotag was applied. Note that the mole 123 appears dark over the faint area 124.

122 is the visible recurring melanoma mole. Note that the region around the mole is indistinguishable from other normal skin on the patient. 125 shows the same mole location under IR light. 126 shows the recurring melanoma bright area around the same mole. Note that the visible portion of the mole also glows within the biotag region, rather than covering it darkly, as in 123. Note that the recurring melanoma region 126 extends significantly past the border of the visible mole 122. Note that the total recurring melanoma area 126 of the patient's skin is visible in FIG. 9*b*.

Figure 10:
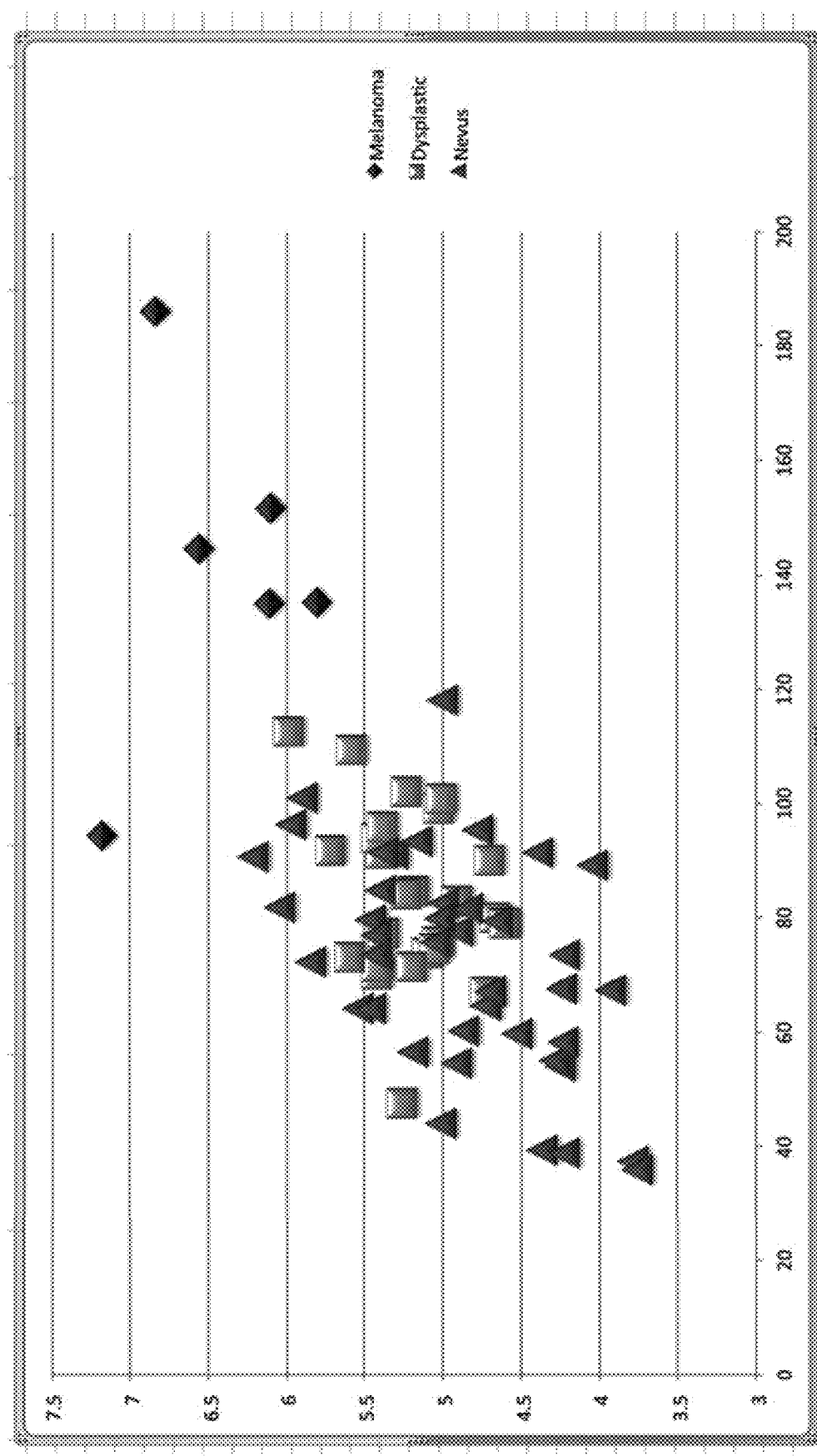
FIG. 10 shows an X-Y graph of two features identified automatically from image analysis of sample images. Three types of moles are shown as different symbols on the graph.

FIG. 10 shows an X-Y plot of two important features from 72 sample images. The X-axis is a texture features approximating the entropy of the mole area. The Y-axis is mean intensity of the biotag fluorescence in the area around the mole. The units shown on the graph are relatively arbitrary units as a function of the specific image processing algorithms used. These two features are two of 28 features automatically determined by image processing of the images. Each of the 72 samples has been medically classified into one of three groups: (a) melanoma, (b) dysplastic, or (c) nevus. There are 6 melanoma samples; 25 dysplastic samples, and 41 nevus samples. The melanoma samples are shown as diamonds; the dysplastic samples are shown as squares; the nevus samples are shown triangles. As can be seen in the Figure, the nevus samples (triangles) tend to clump in the lower left; the dysplastic samples tend to clump in the center; and the melanoma samples in the upper right.

Figure 11:
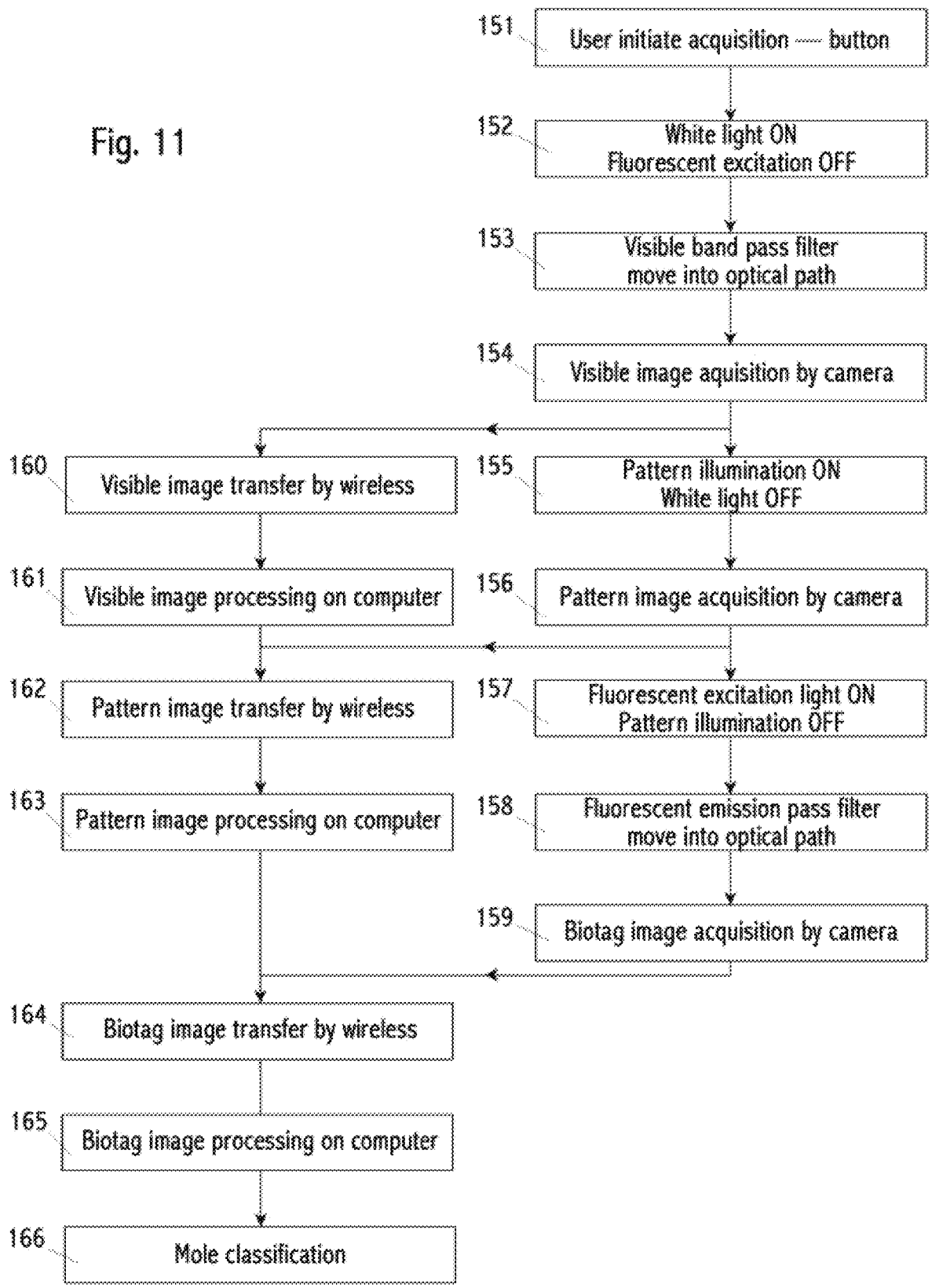
FIG. 11 shows a flowchart of image processing.

FIG. 11 is a flow chart of several embodiments of image acquisition, image processing through to mole classification. Each step is labeled within the box for that step and is discussed in detail previously. Step 151 begins the sequence with the user pressing a button or equivalent operation. Steps 152, 153 and 154 complete the acquisition of the visible light image. The sequence then continues, depending on the embodiment, with steps.

One way to present data of this form to a medical professional is to show the physician on a plot like this the specific patient samples of interest. Typically, the baseline of known samples would be much larger than the 72 sample images seen here. The physician could then make his her own judgment, based on the X-Y position of the patient's images on the chart, of the relative risk to the patient, diagnosis and treatment options. In another embodiment the invention provides a set of numerical metrics to the physician representing either distance on the chart or computed likelihood that the patient sample is in one of these categories.

In one embodiment a series of areas, such as an ellipse, are placed around each group of related moles. The areas represent probabilities, such as 50% or 90% that a mole of a particular type falls within that area. Then, for each patient image, a normalized metric is provided to the physician representing the quality of fit for that patient image within the most likely or most interesting areas. Thus, the medical professional is provided with consistently produced metrics from the automated image analysis, while the medical professional continues to make decisions requiring medical judgment.

Of course many more relationships between the features are identified, typically using multi-variant analysis. Some of these relationships have higher dimensionality than 2D (X v. Y). The scores for multiple feature relationships may be aggregated to produce a small number of simple metrics, such as the probability that a particular patient image is nevus, dysplastic or melanoma.

FIG. 12 shows an image of a mole 202 with structured illumination lines 203. The skin around the mole is shown 201. Two or ideally more straight lines 203 are projected across the skin 201 and the mole 202. The lines 203 are shown in this image as black, for clarity, although in a preferred embodiment they are white light, or monochromatic light such as from an LED or laser. As the structured illumination lines 203 cross the textured, raised, lowered, bumpy or mottled surface of the mole 202 they deform 204 from straight. These deformations 204 show the relative height of that portion of the mole. The structured illumination lines 203 are projected onto the mole 202 and skin 201 from an angle relative to the angle of the camera to the mole, for the camera or optics that are used to create this image. The known geometry of the illumination, camera and mole are used to compute the height (elevation) of the mole at each point of each line where it crosses the mole. Statistical analysis of these aggregated elevations is then used as part of the classification algorithm, discussed elsewhere herein. For example, minimum, maximum, average, spacing of bumps, height of bumps, and other metrics are readily computed from the aggregate elevations.

Figure 13:
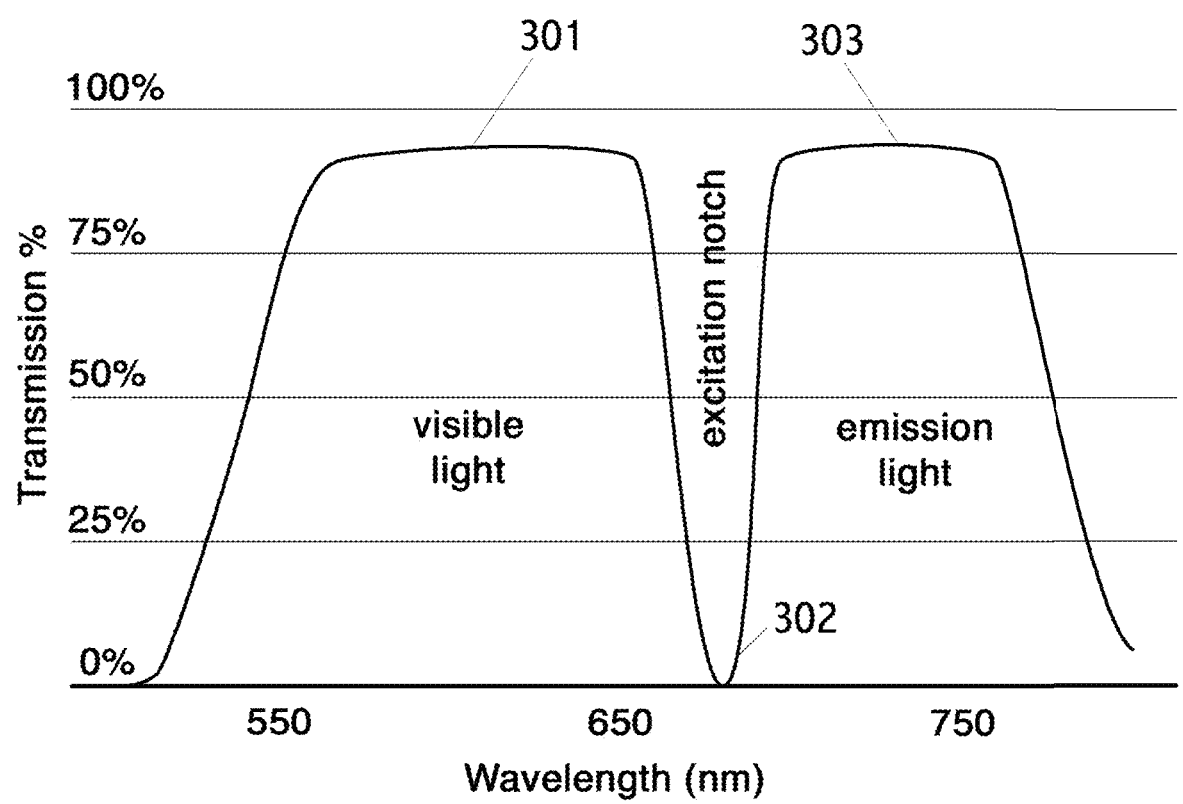
FIG. 13 shows an exemplary curve for a single, hybrid filter.

FIG. 13 shows an exemplary optical transmission curve for a single filter used in one embodiment. This filter employs a notch filter 302 at the same wavelength as the emission light. The filter is a band pass for both visible light 301, or most visible light, and for the emission light 303. The use of this single filter, rather than two filters, is discussed in the text above. Any number of filters may be employed with various band passes for various wavelengths. In some instances, no overlap may be provided the transmitted wavelengths between the different filters. Alternatively, some overlap may occur.

Another embodiment uses a third provided light source, rather than fiducials, for the autofocusing step at the emission wavelength. In this embodiment, rather than fiducials (or, in addition to fiducials), the area of interest is illuminated by light in the emission spectra of the biotag, such as by LEDs, or by a light source with a narrow-pass-band filter. The autofocus of the camera is then used to focus on the area of interest at this wavelength. Then, this "autofocus" light is turned off, the excitation-band light source is turned on, and the exposure is taken. This exposure comprises emission-band light from the biotag and is still in focus at this wavelength.

Gel formulations may comprise DMSO; Ethanol, 200 proof or Propylene Glycol or Propylene Glycol or Glycerine; Hydroxypropyl cellulose, HF (Klucel) or Carbopol 980 or Carbopol 971 or carbomer; Trolamine. For example, a formulation may comprise DMSO 45 w/w, Glycerine 55.87 w/w, Carbopol 9801 w/w, Trolamine 0.13 w/w. In alternative formulations the solvent is replaced with saline or a non-aqueous solution, e.g. MSM—methylsulfonylmethane. Alternative gelling agents include Methocel or Kucel, Carbopol 971 or carbomer.

It should be understood from the foregoing that, while particular implementations have been illustrated and described, various modifications can be made thereto and are contemplated herein. It is also not intended that the invention be limited by the specific examples provided within the specification. The descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method comprising an imaging an area of interest comprising a first area and a second area on a surface of an individual wherein the first area comprises a lesion, the imaging comprising:
   a biotag to the area of interest;
   capturing a visible an image of the area of interest in a visible mode;
   capturing a fluorescent image of the area of interest in a fluorescent mode;
   and
   obtaining features of the lesion by combining the visible image and the fluorescent image.

2. The method of claim 1, wherein the surface is selected from skin, cervix, oral mucosal surfaces, and bladder.

3. The method of claim 1, wherein the biotag binds to the first area and/or the second area, and wherein the first area comprises tumor cells and the second area comprises a tumor macroenvironment.

4. The method of claim 1, further comprising providing a fluorescent fiducial to the area of interest.

5. The method of claim 1 wherein the biotag comprises a detectable label that is detectable in a selected range of wavelengths.

6. The method of claim 5 wherein the detectable label is a fluorescent dye.

7. The method of claim 1, wherein the biotag comprises a first fluorescence dye conjugated with one or more cancer sensitive biological entities selected from protein, RNA, and DNA.

8. The method of claim 7, wherein the biotag comprises Cy5.5 as a detectable marker.

9. A method of claim 1 further comprising:
   illuminating the area of interest to generate a structure illumination;
   autofocusing an integrated imaging device on the structure illumination;
   imaging the structure illumination to calculate a three-dimensional image of the first area;
   illuminating the area of interest with a fluorescent excitation wavelength;
   imaging an fluorescent emission to obtain a fluorescent light image;
   illuminating the area of interest with white light;
   imaging in white light to obtain a white light image;
   measuring an attribute of the first area using automated image processing of a three-dimensional image obtained from the white light image and the fluorescent light image;
   inputting the measurement as input to software; and
   detecting a cancerous or pre-cancerous lesion from the three-dimensional image.

10. The method of claim 9, wherein the integrated imaging device comprises:

an image sensor, an autofocus control logic, an embedded processor with memory for stored instructions and one or more of: (i) a lens, or (ii) a lens mount adapted to accept a lens; such that a field of view of the integrated imaging device includes the area of interest.

11. The method of claim 10, wherein the step of imaging fluorescent emission comprises:
activating a user control on the integrated imaging device to initiate an imaging sequence, where the imaging sequence comprises:
  illuminating the area of interest by an emission light source in an optical band that overlaps with an emission optical band of the biotag;
  autofocusing by the autofocus control logic within the integrated imaging device on the field of view and turn off autofocus illumination while maintaining a focus position and illuminating the area of interest by an excitation light source in an optical band that overlaps an excitation optical band of the biotag; and
exposing the integrated imaging device to the field of view.

12. The method of claim 1, further comprising:
placing a fiducial next to the lesion; and
detecting the fiducial in a three-dimensional image and registering with the visible image and the fluorescent images.

13. The method of claim 1, wherein the step of capturing an image of the area of interest comprises:
  placing an integrated imaging device comprising: an internal image sensor, internal autofocus control logic, internal embedded processor with memory for stored instructions and one or more of: (i) a lens, or (ii) a lens mount adapted to accept a lens; such that a field of view of the integrated imaging device includes the first area and the second area of the area of interest;
  activating a user control on the integrated imaging device to initiate a first imaging sequence, where the first imaging sequence comprises:
    illuminating the area of interest by an excitation light source in an optical band that overlaps an excitation optical band of the biotag;
    autofocusing by the autofocus control logic within the integrated imaging device on the field of view; and
    exposing the integrated imaging device to the field of view.

14. The method of claim 13 wherein the fiducial comprises at least one mark used as a focus target in autofocusing.

15. The method of claim 13, further comprising:
determining an auto-exposure setting, wherein the fiducial further comprises at least one calibrated exposure mark, and wherein the auto-exposure setting uses the at least one calibrated exposure mark;
automatically numerically measuring a quantity of the biotag in the area of interest using the at least one calibrated exposure mark; and
presenting to a medical service a numerical measurement of the quantity of the biotag at a same time as at least one of the images produced by the first and second imaging sequences.

16. The method of claim 1, wherein the fiducial comprises:
  a base that is not visible in a predetermined emission spectra when exposed to light in a predetermined excitation spectra comprising:
    a fluorescent calibration mark with a predetermined calibration brightness in the predetermined emission spectra when exposed to light in a predetermined excitation light spectra, wherein this mark comprises a solid area,
    a fluorescent focus mark with sharply defined borders adapted for use by an autofocus mechanism of an integrated optical system;
    a pair of measurement marks with predetermined spacing;
    a fluorescent alignment mark visible in both visible light and visible in light in the predetermined emission spectra when exposed to light in the predetermined excitation spectra wherein this mark is not circularly symmetric; and
  a direction mark adapted to identify at least one anatomical term of location for a patient.

17. The method of claim 1, wherein the lesion comprises a cavity surface or a tissue surface comprising a lesion suspected to be cancerous or pre-cancerous and the second area comprises an area surrounding the first area.

18. The method of claim 1, further comprises segmenting the visible image to find a border of the first area.

19. The method of claim 18, further comprises extracting a color and a texture from the visible image.

20. The method of claim 1, wherein a fiducial locator combines the visible image and the fluorescent image.

21. The method of claim 1, further comprises an imaging of the area of interest in an emission spectrum before application of the biotag in the first area.

22. A method of imaging an area of interest on skin of an individual the method comprising:
  applying topically to the skin, in an area of interest comprising a lesion suspected to be cancerous or pre-cancerous a specific binding partner that binds to a targeted molecule of interest wherein the specific binding partner is a polypeptide of less than 10.000 daltons;
  capturing a visible image of the area of interest in a visible mode;
  capturing a fluorescent image of the area of interest in a fluorescent mode;
  obtaining features of the lesion by combining the visible image and the fluorescent image.

23. The method of claim 22, further comprising:
placing a fiducial next to the lesion; and
detecting the fiducial in a three-dimensional image and using fiducial dimensions to correct for magnification effects between the visible image, the fluorescent image and the three-dimensional image.

* * * * *